(12) United States Patent
Qing

(10) Patent No.: US 12,241,857 B2
(45) Date of Patent: Mar. 4, 2025

(54) HIGH DENSITY AND MULTIPLEXED NANOPORE DEVICES WITH TRANSVERSE TUNNELING JUNCTION FOR BIOMOLECULE DETECTION AND SEQUENCING

(71) Applicant: ARIZONA BOARD OF REGENTS ON BEHALF OF ARIZONA STATE UNIVERSITY, Scottsdale, AZ (US)

(72) Inventor: Quan Qing, Chandler, AZ (US)

(73) Assignee: Arizona Board of Regents on Behalf of Arizona State University, Scottsdale, AZ (US)

( * ) Notice: Subject to any disclaimer, the term of this patent is extended or adjusted under 35 U.S.C. 154(b) by 0 days.

(21) Appl. No.: 18/550,881

(22) PCT Filed: Mar. 15, 2022

(86) PCT No.: PCT/US2022/020441
§ 371 (c)(1),
(2) Date: Sep. 15, 2023

(87) PCT Pub. No.: WO2022/197741
PCT Pub. Date: Sep. 22, 2022

(65) Prior Publication Data
US 2024/0151682 A1 May 9, 2024

Related U.S. Application Data

(60) Provisional application No. 63/161,681, filed on Mar. 16, 2021.

(51) Int. Cl.
*G01N 27/327* (2006.01)
*B01L 3/00* (2006.01)

(52) U.S. Cl.
CPC .... *G01N 27/3278* (2013.01); *B01L 3/502707* (2013.01); *B01L 2300/0645* (2013.01);
(Continued)

(58) Field of Classification Search
None
See application file for complete search history.

(56) References Cited

U.S. PATENT DOCUMENTS 7,670,772 B2   3/2010   Kim et al.
7,906,345 B2   3/2011   Wang et al.
(Continued)

FOREIGN PATENT DOCUMENTS

CN    103055973 A    4/2013
CN    107661783 A    2/2018
(Continued)

OTHER PUBLICATIONS

Wang, Y., et al., "Nanopore chip with self-aligned transverse tunneling junction for DNA detection", Biosensors and Bioelectronics, Aug. 9, 2021, pp. 1-7, vol. 193, No. 113552, Elsevier B.V.
(Continued)

*Primary Examiner* — J. Christopher Ball
(74) *Attorney, Agent, or Firm* — Lewis Roca Rothgerber Christie LLP

(57) ABSTRACT

Disclosed are systems and methods for delivering and/or linking molecules, such as DNA, between tunable metal nanogaps and measuring electrical and/or optical properties. In one example, disclosed are high density multiplexed chips with a plurality of groups, each group including a plurality of nanodevices, the chips capable of coupling to one or more multiwell structures for providing samples to each individual group. In this way, the chips can be used for high-throughput analysis of molecules such as DNA.

27 Claims, 13 Drawing Sheets

(52) U.S. Cl.
CPC ............... *B01L 2300/0896* (2013.01); *B01L 2400/0415* (2013.01)

(56) References Cited

U.S. PATENT DOCUMENTS

| | | | |
|---|---|---|---|
| 8,318,093 | B2 | 11/2012 | Wang et al. |
| 9,810,680 | B2 | 11/2017 | Chou et al. |
| 9,903,820 | B2 | 2/2018 | Meller et al. |
| 9,921,181 | B2 | 3/2018 | Baldauf et al. |
| 10,065,154 | B2 | 9/2018 | Aguilar et al. |
| 2010/0267158 | A1 | 10/2010 | Chou et al. |
| 2011/0063758 | A1 | 3/2011 | Wang et al. |
| 2012/0193236 | A1 | 8/2012 | Peng et al. |
| 2013/0119497 | A1 | 5/2013 | Li |
| 2013/0142708 | A1 | 6/2013 | Battrell et al. |
| 2014/0099726 | A1 | 4/2014 | Heller |
| 2014/0190833 | A1 | 7/2014 | Lieber et al. |
| 2014/0251825 | A1 | 9/2014 | Van Der Voorn et al. |
| 2015/0010935 | A1 | 1/2015 | Lindsey et al. |
| 2015/0211059 | A1 | 7/2015 | Reinhart et al. |
| 2015/0377830 | A1 | 12/2015 | Baldauf et al. |
| 2016/0025702 | A1 | 1/2016 | Lindsay et al. |
| 2017/0199149 | A1 | 7/2017 | Gundlach et al. |
| 2018/0275088 | A1 | 9/2018 | Huff et al. |
| 2018/0280968 | A1 | 10/2018 | Qing et al. |
| 2018/0298436 | A1 | 10/2018 | Lei et al. |
| 2019/0071720 | A1 | 3/2019 | Nordman et al. |

FOREIGN PATENT DOCUMENTS

| | | |
|---|---|---|
| EP | 2 195 461 B1 | 6/2010 |
| EP | 3 391 037 A1 | 6/2017 |
| EP | 3 391 037 B1 | 6/2022 |
| JP | 2007-506432 A | 3/2007 |
| JP | 2018-533935 A | 11/2018 |
| JP | 2020-520446 A | 7/2020 |
| KR | 10-0682920 B1 | 2/2007 |
| KR | 10-2011-102652 A | 9/2011 |
| WO | WO 2005/030997 A1 | 4/2005 |
| WO | WO 2018/192940 A1 | 10/2018 |
| WO | WO 2020/131103 A1 | 6/2020 |
| WO | WO 2022/010935 A2 | 1/2022 |
| WO | WO 2022/055604 A2 | 3/2022 |

OTHER PUBLICATIONS

International Search Report of PCT/US2022/020441, Aug. 15, 2022, 4 pages.
Written Opinion of the International Searching Authority for PCT/US2022/020441, Aug. 15, 2022, 5 pages.
Albrecht, T., "Single-Molecule Analysis with Solid-State Nanopores", Annual Reviews, Feb. 1, 2019, 19 pages.
Bayley, H., "Nanopore Sequencing: From Imagination to Reality", Clinical Chemistry, 2015, vol. 61, No. 1., pp. 25-31.
Branton, D., et al., "The potential and challenges of nanopore sequencing", Nature Biotechnology, Oct. 9, 2008, vol. 26., No. 10., pp. 1146-1153.
Chen, K., "Direction-and Salt-Dependent Ionic Current Signatures for DNA Sensing with Asymmetric Nanopores", Biophysical Journal, Feb. 28, 2017, vol. 112., pp. 674-682.
Di Fiori, N., et al., "Optoelectronic control of surface charge and translocation dynamics in solid-state nanopores", Nature Nanotechnology, Nov. 3, 2013, vol. 8., p. 946-951.
Di Ventra, M., et al. "Decoding DNA, RNA and peptides with quantum tunnelling", Nature Nanotechnology, Feb. 3, 2016, vol. 11., pp. 117-126.
Fischbein, M., et al., "Electron Beam Nanosculpting of Suspended Graphene Sheets", Department of Physics and Astronomy, University of Pennsylvania, Sep. 16, 2008, pp. 1-11.
Fologea, D., et al., "Slowing DNA Translocation in a Solid-State Nanopore", Nano Letters, Jun. 7, 2005, vol. 5, No. 9, pp. 1734-1737.
Fuller, C., et al., "Real-time single-molecule electronic DNA sequencing by synthesis using polymer-tagged nucleotides on a nanopore array", PNAS, May 10, 2016, vol. 113, No. 9, pp. 5233-5238.
Garaj, S., et al., "Graphene as a subnanometre trans-electrode membrane", Nature, Sep. 9, 2010, vol. 467, pp. 190-195.
Hall, J. "Letter to the Editor", The Journal of General Physiology, Jun. 6, 1975, vol. 66, pp. 531-532.
Healy, K., et al., "Fabrication and characterization of nanopores with insulated transverse nanoelectrodes for DNA sensing in salt solution", Electrophoresis, Aug. 9, 2012, vol. 33, pp. 3488-3496.
Heerema, S., et al., "Graphene nanodevices for DNA sequencing", Nature Nanotechnology, Feb. 3, 2016, vol. 11, pp. 127-136.
Huang, S., et al., "Identifying single bases in a DNA oligomer with electron tunnelling", Nature Nanotechnology, Dec. 2010, vol. 5., pp. 868-873.
International Search Report and Written Opinion of the International Searching Authority, mailed Feb. 14, 2022, corresponding to PCT/US21/40568, 11 pages.
International Search Report and Written Opinion of the International Searching Authority, mailed Apr. 5, 2022, corresponding to PCT/US21/40562, 15 pages.
Ip, C., et al., "MinION Analysis and Reference Consortium: Phase 1 data release and analysis [version 1; referees: 2 approved]", F1OOO Research, Oct. 15, 2015, pp. 1-35.
Ivanov, A., et al., "DNA Tunneling Detector Embedded in a Nanopore", Nano Letters, 2011, vol. 11, pp. 279-285.
Ivanov, A., et al., "High Precision Fabrication and Positioning of Nanoelectrodes in a Nanopore", ACS Nano, 2014, vol. 8, No. 2, pp. 1940-1948.
Jain, M., et al., "Improved data analysis for the MinION nanopore sequencer", Nature Methods, Apr. 2015, vol. 12, No. 4, pp. 351-358.
Jain, M., et al., "MinION Analysis and Reference Consortium: Phase 2 data release and analysis of R9.0 chemistry [version 1; referees: 1 approved, 2 approved with reservations]", F1OOO Research, Jul. 28, 2017, pp. 1-18.
Janda, J., et al., "Evolving Concepts Regarding the Genus Aeromonas: An Expanding Panorama of Species, Disease Presentations, and Unanswered Questions", Aeromonas Infections, Aug. 27, 1998, pp. 332-344.
Kasianowicz, J., et al., "Characterization of individual polynucleotide molecules using a membrane channel", Biophysics, Nov. 1996, vol. 93, pp. 13770-13773.
Krishnakumar, P. et al. "Slowing DNA Translocation through a Nanopore Using a 38 Functionalized Electrode", ACS Nano, 2013, 16 pages.
Larkin, J., et al., "Slow DNA Transport through Nanopores in Hafnium Oxide Membranes", ACS Nano, 2013, vol. 7, No. 11, pp. 10121-10128.
Laszlo, A., et al., "Decoding long nanopore sequencing reads of natural DNA", Nature Biotechnology, Aug. 2014, vol. 32., No. 8, pp. 829-834.
Li, J., et al., "Ion-beam sculpting at nanometre length scales", Nature, Jul. 12, 2001, vol. 412, pp. 166-169.
Liang, X., et al., "Nanogap Detector Inside Nanofluidic Channel for Fast Real-Time Label-Free DNA Analysis", Nano Letters, 2008, vol. 8, No. 5, pp. 1472-1476.
Lindsay, S., "The promises and challenges of solid-state sequencing", Nature Nanotechnology, Feb. 2016, vol. 11, pp. 109-111.
Luan, B., et al., "Dynamics of DNA translocation in a solid-state nanorpore immersed in aqueous glycerol", Nanotechnology, 2012, vol. 23, 7 pages.
Meller, A., et al., "Rapid nanopore discrimination between single polynucleotide molecules", PNAS, Feb. 1, 2000, vol. 97, No. 3, pp. 1079-1084.
Mikheyev, A., et al., "A first look at the Oxford Nanopore MinION sequencer", Molecular Ecology, 2014, vol. 14, pp. 1097-1102.
Mueller, M., et al., "The structure of a cytolytic a-helical toxin pore reveals its assembly mechanism", Nature, Jun. 4, 2009, vol. 459, pp. 726-731.
Naaman, R., et al., "Chiral molecules and the electron spin", Nat. Rev. Chem. 3, 250-260, Mar. 25, 2019, https://doi.org/10.1038/s41570-019-0087-1, 27 pages.

(56) References Cited

OTHER PUBLICATIONS

Naaman, R., et al., "Spintronics and Chirality: Spin Selectivity in Electron Transport Through Chiral Molecules", The Annual Review of Physical Chemistry, Jan. 19, 2015, pp. 263-284.

Nam, S-W., et al., "Ionic Field Effect Transistors with Sub-10 nm Multiple Nanopores", Nano Letters, 2009, vol. 9, No. 5, pp. 2044-2048.

Niederweis, M., "Mycobacterial porins—new channel proteins in unique outer membranes", Molecular Microbiology, 2003, vol. 49, No. 5, pp. 1167-1177.

Qing, Q. et al. "Finely Tuning Metallic Nanogap Size with Electrodeposition by Utilizing High-Frequency Impedance in Feedback", Nanotechnology, 2005, 5 pages.

Quick, J., et al., "Real-time, portable genome sequencing for Ebola surveillance", Nature, Feb. 11, 2016, vol. 530, pp. 228-245.

Sadar, J. "Top-down and bottom-up strategies to prepare nanogap sensors for controlling and characterizing single biomolecules", a dissertation, Arizona State University, https://www.proquest.com/docview/2288107671, 2019, 24 pages.

Sadar, J. et al. "Confined Electrochemical Deposition in Sub-15 nm Space for Preparing 31-32 Nanogap Electrodes", ECS Transactions, 2017, 9 pages.

Shi, W., et al., "Nanopore Sensing", Analytical Chemistry, 2017, vol. 89, pp. 157-188.

Song, L., et al., "Structure of Staphylococcal α-Hemolysin, a Heptameric Transmembrane Pore", Science, Dec. 13, 1996, vol. 274, pp. 1859-1867.

Storm, A.J., et al., "Fabrication of solid-state nanopores with single-nanometre precision", Nature Materials, Aug. 2003, vol. 2, pp. 537-541.

Subbarao, G., et al., "Crystal Structure of the Monomeric Porin OmpG", JMB, 2006, vol. 360, pp. 750-759.

Taniguchi, M., et al., "Fabrication of the gating nanopore device", Applied Physics Letters, 2009, vol. 95, 4 pages.

Tsutsui, M., et al., "Identifying single nucleotides by tunnelling current", Nature Nanotechnology, Apr. 2010, vol. 5, pp. 286-290.

Tsutsui, M., et al., "Single-molecule sensing electrode embedded in-plane nanopore", Scientific Reports, Jul. 28, 2011, vol. 1. No. 46, 6 pages.

Tsutsui, M., et al., "Transverse electric field dragging of DNA in a nanochannel", Scientific Reports, May 3, 2012, vol. 2, No. 394, 7 pages.

Venkatesan, B.M., et al., "Highly Sensitive, Mechanically Stable Nanopore Sensors for DNA Analysis", Advanced Materials, 2009, vol. 21, pp. 2771-2776.

Venkatesan, B.M., et al., "Nanopore sensors for nucleic acid analysis", Nature Nanotechnology, Oct. 2011, vol. 6, pp. 615-624.

Wang, Y., et al., "Scalable nanopore chip with self-aligned transverse tunneling junction for DNA detection and sequencing", ACS Sensors, Submitted by Authors on Oct. 2, 2020, 17 pages.

Wanunu, M., "Nanopores: A journey towards DNA sequencing", Physics of Life Reviews, 2012, vol. 9, pp. 125-158.

Wanunu, M., et al., "Electrostatic focusing of unlabelled DNA into nanoscale pores using a salt gradient", Nature Nanotechnology, Feb. 2010, vol. 5, pp. 106-165.

Wendell, D., et al., "Translocation of double-stranded DNA through membrane-adapted phi29 motor protein nanopores", Nature Nanotechnology, Nov. 2009, vol. 4, pp. 765-772.

Zhou, J., et al., "Enhanced nanochannel translocation and localization of genomic DNA molecules using three-dimensional nanofunnels", Nature Communications, 2017, vol. 8, No. 807, pp. 1-8.

Japanese Office Action issued in corresponding Application No. JP 2023-557158, dated Aug. 27, 2024, 3 pages.

Partial English Translation of Japanese Office Action issued in corresponding Application No. JP 2023-557158, dated Aug. 27, 2024, 4 pages.

European Patent Office Extended European Search Report, for Patent Application No. EP 22772090.1, mailed Jan. 2, 2025, 9 pages

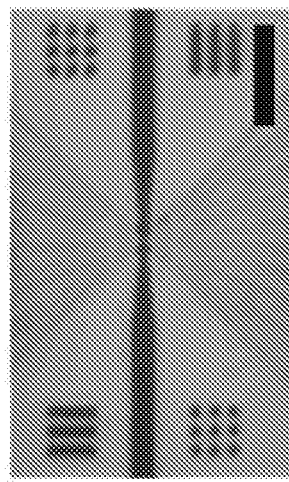 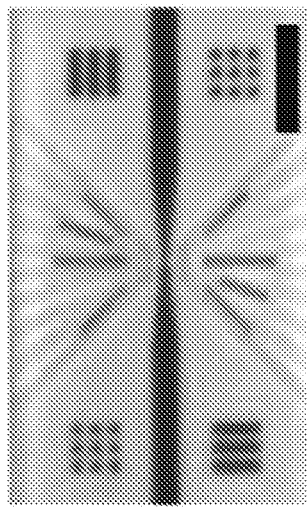
FIG. 4A
FIG. 4B
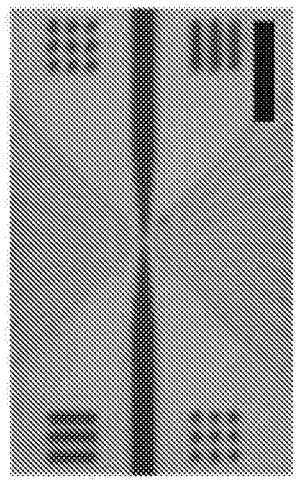 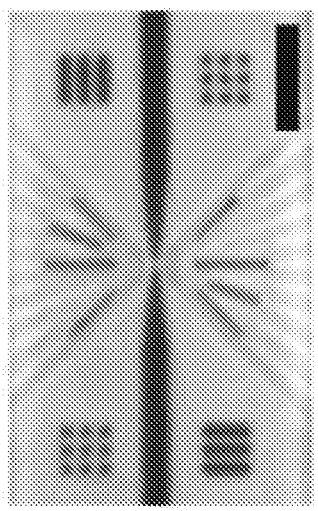

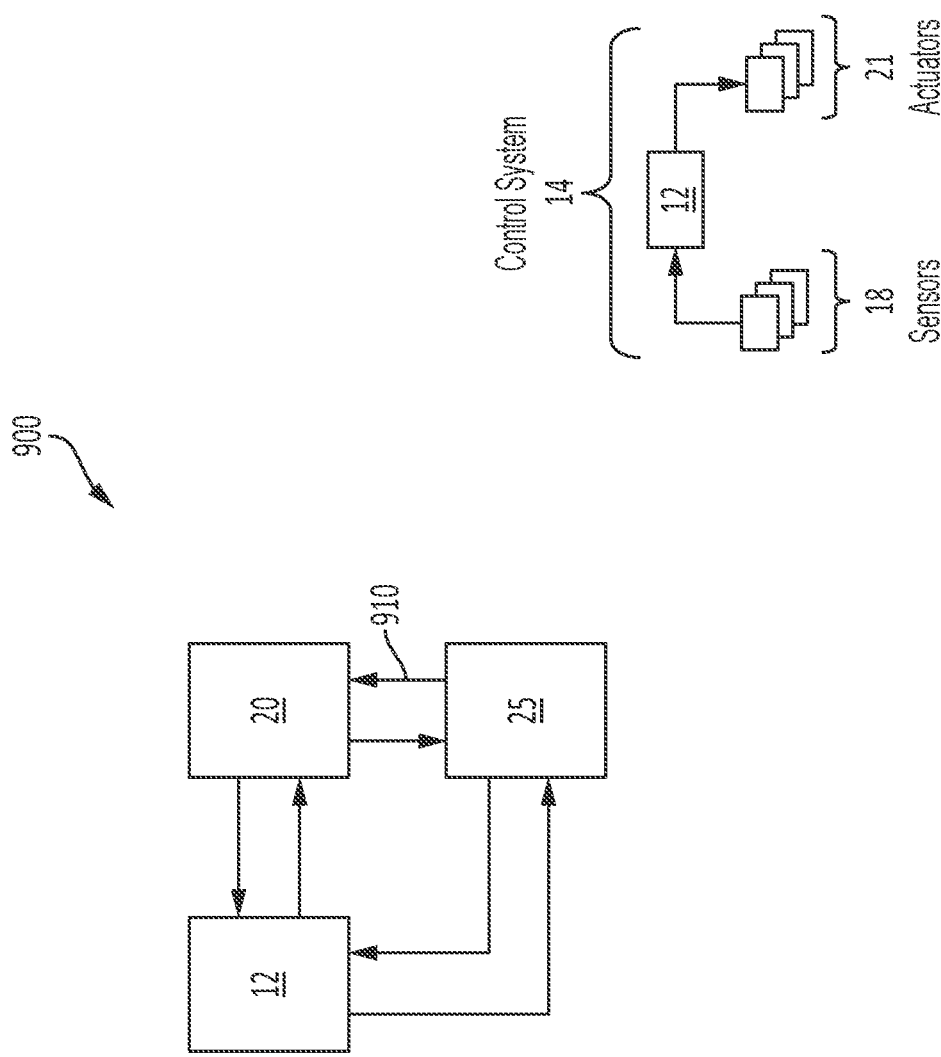

HIGH DENSITY AND MULTIPLEXED NANOPORE DEVICES WITH TRANSVERSE TUNNELING JUNCTION FOR BIOMOLECULE DETECTION AND SEQUENCING

CROSS-REFERENCE TO RELATED APPLICATIONS

The present application is a U.S. national stage entry, under 35 U.S.C. § 371, of International Application Number PCT/US2022/020441, filed on Mar. 15, 2022, which claims priority to and the benefit of U.S. Provisional Application No. 63/161,681, filed Mar. 16, 2021, entitled "HIGH DENSITY AND MULTIPLEXED NANOPORE DEVICES WITH TRANSVERSE TUNNELING JUNCTION FOR BIOMOLECULE DETECTION AND SEQUENCING," the entire content of each of which is incorporated herein by reference.

GOVERNMENT LICENSE RIGHTS

This invention was made with government support under FA9550-16-1-0052 awarded by the Air Force Office of Scientific Research. The government has certain rights in the invention.

FIELD

This disclosure relates to single molecule detection, and in particular, to systems and methods for fabricating and using nanopore devices with transverse tunneling junctions.

BACKGROUND

Nanopore sequencing represents a promising direction for rapid single-molecule level sequencing and characterization techniques. Biological nanopores based on membrane protein channels and their bioengineered mutants can provide atomic-level reproducibility of geometry and size that can be engineered to match the diameter of biomolecules (e.g., DNA) to achieve slower translocation speeds and higher contrast of ionic current, yet challenges remain in terms of signal quality and resolution. These challenges have inspired quantum tunneling-based detection which requires integration of solid-state nanopores with tunneling junctions. However, existing approaches lack precision and reproducibility, resulting in little success. There is thus a need to improve quantum tunneling-based detection techniques, and to develop fabrication strategies that enable increased density of solid-state nanopores on a single chip for parallel processing of samples to achieve high throughput analytical potential.

SUMMARY

Disclosed herein are devices, systems, methods of making, and uses thereof for measuring the electrical and/or optical properties of single molecules using tunable metal nanogaps embedded into a nanofluidic system. The manner of making the devices of the present disclosure enables fabrication of single chips with high density arrays of nanodevices (also referred to as electronic devices, or electronic nanodevices) as described herein. The nanodevices can be grouped into distinct groups on a single chip, thereby providing an ability to effectively provide different samples to different groups, for high-throughput analysis of the electrical and/or optical properties of the molecules corresponding to the different samples. In embodiments, translocation and/or mounting/linking events between molecules and the electrodes that comprise the tunable metal nanogaps can be characterized based on ionic current traces between a top chamber and a bottom chamber with the nanogap positioned therebetween, and/or based tunneling currents measured by way of the nanogap electrodes, and/or based on optical properties of said molecules.

Thus, in one aspect, an electronic device comprises a top fluidic channel/chamber and a bottom fluidic channel/chamber fabricated on a planar substrate, the top fluidic channel/chamber including a first open window at a top of the electronic device but sealed at a bottom of the electronic device, and the bottom fluidic channel/chamber including a second open window at the bottom of the electronic device but sealed at the top of the electronic device. The electronic device further includes a first electrode and a second electrode positioned in a space of the electronic device between the top fluidic channel/chamber and the bottom fluidic channel/chamber. The electronic device further includes a nanogap having dimensions determined in part by a distance between the first electrode and the second electrode, where the distance is defined via the first and the second electrodes being electrochemical deposited under feedback control with one or more metal materials within the top fluidic channel/chamber and/or the bottom fluidic channel/chamber, thereby forming the electronic device with a single path for a molecule to travel from the top fluidic channel/chamber to the bottom fluidic channel/chamber, or vice versa. The distance between the first electrode and the second electrode is between about 1-100 nm, and the nanogap is self-aligned and has a narrowest bottleneck in the single path between the top fluidic channel/chamber and the bottom fluidic channel.

In one aspect a method to measure electronic and/or optical properties from single molecules, comprises detecting with an electronic device as herein disclosed an individual mounting and/or translocation event of single molecules by a correlated ionic current between the top fluidic channel/chamber and the bottom fluidic channel/chamber, and a tunneling current between the first and second electrodes through the nanogap, and performing electrical and/or optical characterization.

In an embodiment, performing electrical and/or optical characterization includes performing Raman spectroscopy by performing tip-enhanced Raman spectrum through a transparent substrate, or from the top side of a non-transparent substrate of the electronic device to characterize a dynamic structure of the single molecules.

In an embodiment, performing electrical and/or optical characterization includes determining a sequence corresponding to the single molecules.

In one aspect, a chip for measuring electrical and/or optical properties from single molecules, comprises a plurality of the electronic devices as herein disclosed. The plurality of electronic devices may be between 2-1000, or between 1000-10000, or may even be greater than 10,000 in some examples.

In embodiments, the plurality of electronic devices are divided into a predetermined number of different groups. In some examples, one or more multiwell structures may be coupled to the chip, with individual wells corresponding to each of the predetermined number of different groups. In some examples, the one or more multiwell structures comprises a first multiwell structure that couples to a top-side of the chip for providing samples to a top fluidic channel/chamber of each of the plurality of electronic devices, and optionally, a second multiwell structure that couples to a bottom-side of the chip for receiving samples initially provided to the top fluidic channel/chamber following translocation of analyte within each of the samples to a bottom fluidic channel/chamber.

In embodiments, the chip may include one or more multiplexers associated with individual groups, for collecting signals simultaneously from electronic devices corresponding to a particular group.

In one aspect, a system for high-throughput analysis of single molecules comprises a chip as herein disclosed with any number of electronic nanodevices as herein disclosed, and a fluidics device capable of delivering individual samples to each of the plurality of different groups. The system further includes a controller storing instructions in non-transitory memory that, when executed, cause the controller to instruct the fluidics device to provide individual samples to one or more of the plurality of different groups, and following the providing, record data comprised of one or more of ionic current between the top fluidic channel/chamber and the bottom fluidic channel/chamber, tunneling current, and/or optical signals from each electronic device corresponding to one or more of the plurality of different groups, the data corresponding to individual mounting/linking and/or translocation events of individual molecules within each electronic device.

In one aspect a method of making an electronic device that includes a nanopore and a tunneling junction, comprises depositing a first sacrificial layer defining a final cavity for electrochemical deposition and depositing a second outer sacrificial layer defining a final nanofluidic space connecting the nanopore to a top fluidic channel/chamber and to a bottom fluidic channel/chamber onto a substrate layer; positioning a pair of electrodes with a spacing of about 600 nm to 2 µm on top of the first sacrificial layer; depositing a passivation layer on top of the pair of electrodes, the first sacrificial layer, the second outer sacrificial layer, and the planar substrate; conducting a dry etching process to remove a first section of the passivation layer and to remove a second section of the substrate layer from a bottom-side of the substrate layer, thereby providing a first window to the second outer sacrificial layer corresponding the top fluidic channel/chamber, and a second window to the second outer sacrificial layer corresponding to the bottom fluidic channel/chamber; chemically etching the first and second sacrificial layers to construct the final nanofluidic space; and narrowing the spacing between the pair of electrodes by a process of controlled electrochemical deposition of a metal onto the pair of electrodes to form the nanopore and the tunneling junction.

The foregoing and other features of the disclosure will become more apparent from the following detailed description, which proceeds with reference to the accompanying figures.

BRIEF DESCRIPTION OF THE DRAWINGS

Embodiments will be readily understood by the following detailed description in conjunction with the accompanying drawings and the appended claims. Embodiments are illustrated by way of example and not by way of limitation in the figures of the accompanying drawings.

FIG. 1B is a single representative event showing the time and polarity correlation between the tunneling current and the ionic current.

FIG. 1C and FIG. 1D show longer time records of translocation happening in both directions as depicted by polarities of the signals. The signals of FIGS. 1B-1D are illustrative examples of the types of signals that can be recorded using devices of the type depicted at FIG. 1A and the electronic devices and chips incorporating said electronic devices of the present disclosure;

FIGS. 4A-4B depict selected frames of time lapse recordings during electrode metal depositions with different deposition pulses;

FIG. 6B is a transparent rendering of the nanodevice depicted at FIG. 6A;

FIG. 9 depicts a high-level exemplary system for automated use of the nanodevices and/or chips of the present disclosure.

DETAILED DESCRIPTION

Figure 1B:
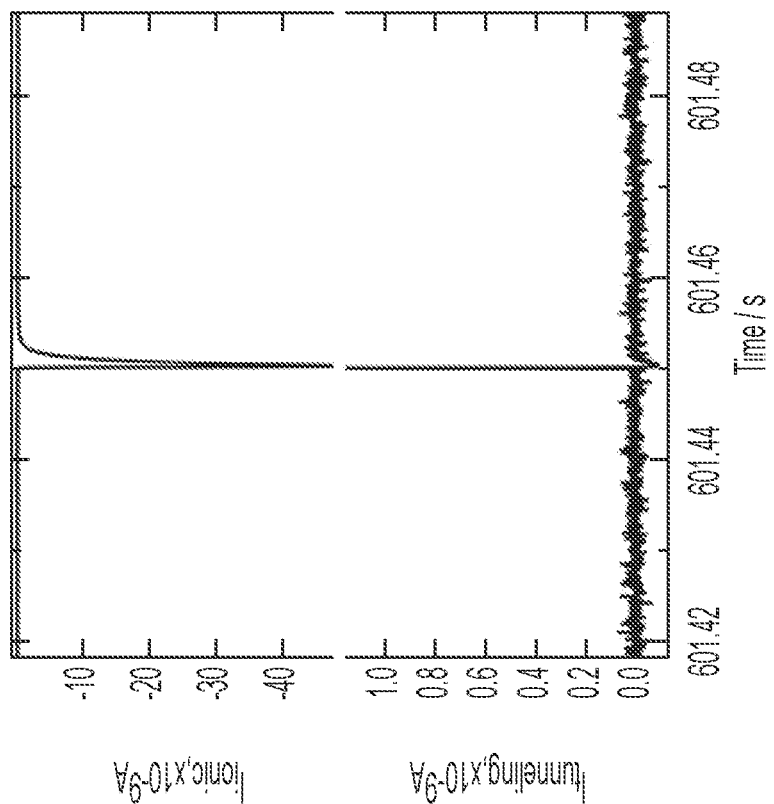
FIGS. 1B-1D illustrate that approximately 100% correlated signals from both the ionic current channel and the tunneling current channel can identify the same DNA translocation events.
Figure 1A:
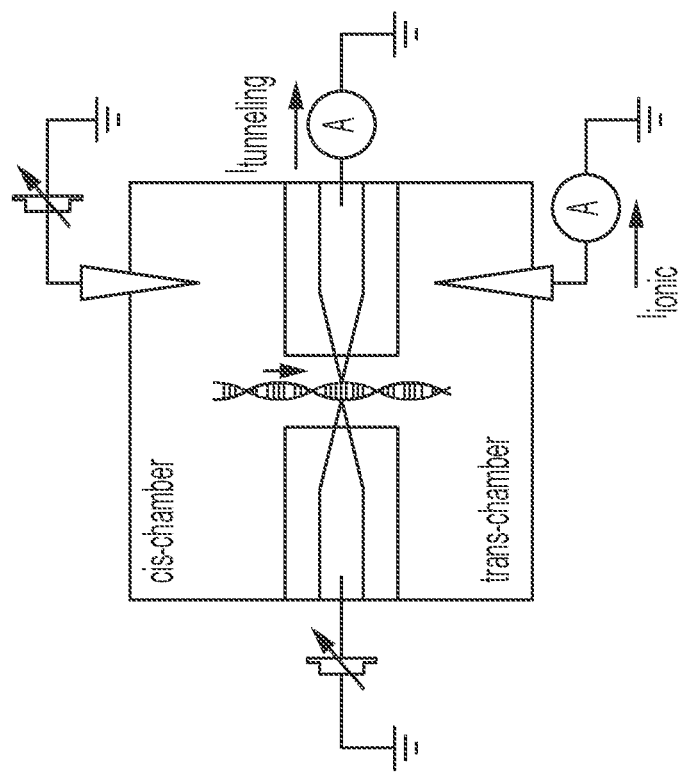
FIG. 1A depicts a high-level illustration of a biomolecule translocation detection circuit. In such a circuit, a biomolecule (e.g., DNA, protein, peptide, small molecule, RNA, mRNA, and the like) is driven from the cis-chamber to the trans-chamber by a bias (e.g., negative bias in the case of DNA), and the ionic current ($I_{ionic}$) is recorded. Simultaneously, a small bias is applied between the transverse electrodes and the current across the tunneling junction ($I_{tunneling}$) is recorded to track the same translocation event. A pair of metal electrodes forms a nanogap through which the biomolecules are driven.
Figure 1C:
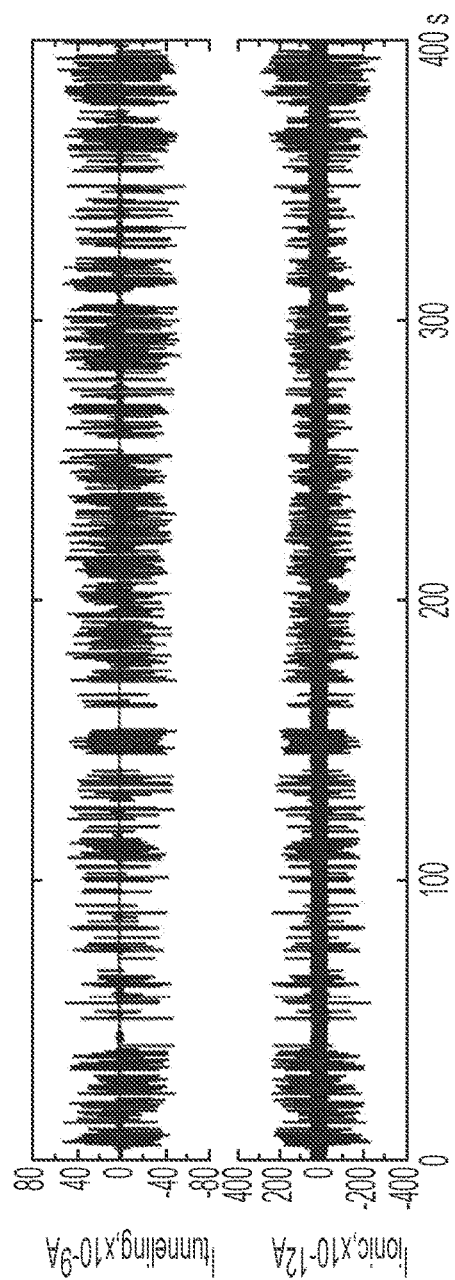
Figure 1D:
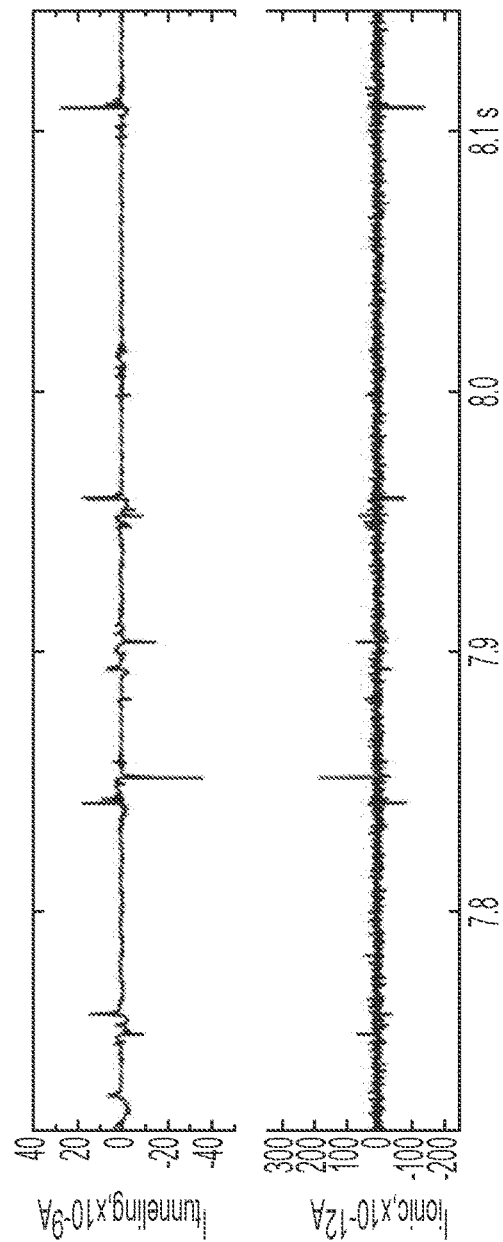

In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense.

Various operations may be described as multiple discrete operations in turn, in a manner that may be helpful in understanding embodiments; however, the order of description should not be construed to imply that these operations are order-dependent.

The description may use perspective-based descriptions such as up/down, back/front, and top/bottom. Such descriptions are merely used to facilitate the discussion and are not intended to restrict the application of disclosed embodiments.

The terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still cooperate or interact with each other.

For the purposes of the description, a phrase in the form "A/B" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the terms "embodiment" or "embodiments," which may each refer to one or more of the same or different embodiments. Furthermore, the terms "comprising," "including," "having," and the like, as used with respect to embodiments, are synonymous, and are generally intended as "open" terms (e.g., the term "including" should be interpreted as "including but not limited to," the term "having" should be interpreted as "having at least," the term "includes" should be interpreted as "includes but is not limited to," etc.).

With respect to the use of any plural and/or singular terms herein, those having skill in the art can translate from the plural to the singular and/or from the singular to the plural as is appropriate to the context and/or application. The various singular/plural permutations may be expressly set forth herein for sake of clarity.

The term "a" or "an" may mean more than one of an item.

The term "about" means within plus or minus 10% of a stated value. For example, "about 100" would refer to any number between 90 and 110. Furthermore, recitation of a range of numerical values includes any numerical value encompassed by said range, and/or any range of values included within said range. For example, a numerical range of 1-10 encompasses the range, and additionally encompasses individual numerical values (e.g., 1, 2, 3, 4, 5, 6, 7, 8, 9, 10), and ranges within said numerical range (e.g., 1-2, 1-4, 2-5, 3-7, 4-9, 5-10, and so on).

Unless otherwise noted, technical terms are used according to conventional usage. Suitable methods and materials for the practice or testing of this disclosure are described below. Such methods and materials are illustrative only and are not intended to be limiting. Other methods and materials similar or equivalent to those described herein can be used. For example, conventional methods well known in the art to which this disclosure pertains are described in various general references.

I. Terms

To facilitate review of the various embodiments of the disclosure, the following explanations of specific terms are provided:

Analyte: A substance whose chemical constituents are being identified and measured. In some examples, an analyte includes DNA, proteins, enzymes, RNA, small molecules, peptides and/or other bio-molecules.

Binding or stable binding: An association between two substances or molecules, such as the association of an antibody with an antigen. Binding can be detected by any procedure known to one skilled in the art, such as by physical or functional properties of the formed complexes.

Biomolecule: A molecule that is produced by a living organism and/or has some level of activity in a living organism. For example, a biomolecule is an organic molecule and especially a macromolecule (such as a protein or nucleic acid) in living organisms. In some examples, biomolecule is interchangeable with "analyte molecule." In some examples, a therapeutic biomolecule can be synthetically produced for use in a living organism.

Chemical Modification: A number of various processes involving the alteration of the chemical constitution or structure of molecules. In one example, a chemically-modified electrode is an electrode that has a surface chemically converted to change the electrode's properties, such as its' physical, chemical, electrochemical, optical, electrical, and/or transport characteristics.

Top chamber and Bottom chamber: A "top chamber" is first chamber and a "bottom chamber" is a second chamber that is opposite to the top chamber, such as on an opposite side of the top chamber. Discussed herein, a top chamber is open to a top side of a nanodevice, whereas a bottom chamber is open to a bottom side of the nanodevice. In embodiments, the top chamber is a chamber with a negative electrode and the bottom chamber on the opposite side of a nanogap is the chamber with a positive electrode such that a negatively charged molecule in the top chamber can be guided through the nanogap to the bottom chamber by a driving bias. Top chamber can also be referred to as "cis-chamber", and bottom chamber can also be referred to as "trans-chamber." In other examples, the potential applied to the top and bottom chambers can be reversed in polarity, i.e., a negative potential applied to the top chamber, and a positive potential applied to the bottom chamber, to reverse the movement of molecules passing through the channel.

Contacting: Placement in direct physical association, including both a solid and liquid form.

Deposit: An accumulation or layer of solid material, either consolidated or unconsolidated, left or laid down.

Dielectric: A dielectric material is a type of insulator which becomes polarized when it comes in contact with an electrical field. When dielectrics are placed in an electric field, practically no current flows in them because, unlike metals, they have no loosely bound, or free, electrons that may drift through the material. Instead, electric polarization occurs.

Electrochemical Deposition: A process by which a thin and tightly adherent desired coating of metal, oxide, or salt can be deposited onto the surface of a conductor substrate by simple electrolysis of a solution containing the desired metal ion or its chemical complex. Electrochemical deposition transports metal ions in a solution by an electric field to coat the surface of a substrate. Electrochemical deposition is an efficient procedure to prepare metal nanoparticles. The process may be reversible. For example, discussed herein, "reversible pulsed electrochemical deposition" refers to a process whereby both deposition and removal of the desired coating is performed any number of times.

Isolated: An "isolated" biological component (such as a nucleic acid molecule, protein, or cell) has been substantially separated or purified away from other biological components in the cell of the organism, or the organism itself, in which the component naturally occurs, such as other chromosomal and extra-chromosomal DNA and RNA, proteins and cells. Nucleic acid molecules and proteins that have been "isolated" may be understood to have been purified by standard purification methods. The term also embraces nucleic acid molecules and proteins prepared by recombinant expression in a host cell as well as chemically synthesized nucleic acid molecules and proteins.

Label: An agent capable of detection, for example, a label can be attached to a nucleic acid molecule or protein (indirectly or directly), thereby permitting detection of the nucleic acid molecule or protein. Examples of labels include, but are not limited to, radioactive isotopes, enzyme substrates, co-factors, ligands, chemiluminescent agents, fluorophores, haptens, enzymes, and combinations thereof. Methods for labeling and guidance in the choice of labels appropriate for various purposes are discussed for example in Sambrook et al. (Molecular Cloning: A Laboratory Manual, Cold Spring Harbor, New York, 1989) and Ausubel et al. (In Current Protocols in Molecular Biology, John Wiley & Sons, New York, 1998).

Linked or linker: The term "linked" means joined together, either directly or indirectly. For example, a first moiety may be covalently or noncovalently (e.g., electrostatically) linked to a second moiety. This includes, but is not limited to, covalently bonding one molecule to another molecule, noncovalently bonding one molecule to another (e.g., electrostatically bonding), non-covalently bonding one molecule to another molecule by hydrogen bonding, non-covalently bonding one molecule to another molecule by van der Waals forces, and any and all combinations of such couplings. Indirect attachment is possible, such as by using a "linker" (a molecule or group of atoms positioned between two moieties).

In several embodiments, linked components are associated in a chemical or physical manner so that the components are not freely dispersible from one another. For example, two components may be covalently bound to one another so that the two components are incapable of separately dispersing or diffusing.

Microfluidics: Discussed herein, "microfluidics" refers to both the behaviour of fluids through micro-channels, and the technology of manufacturing microminiaturized devices containing chambers and tunnels through which fluids flow or are confined. Microfluidics relates to small volumes of fluids, down to femtoliters. Discussed herein "microfluidics device" or "microfluidics system" refers to manufactured structures (e.g., microfluidics chips) with any number of micro-channels etched or molded into a material (e.g., glass, silicon, PDMS, and the like). A "microfluidics system" refers to a microfluidics device that incorporates other aspects including but not limited to a pump, pressure regulators, and the like. Microfluidics devices/systems are encompassed by the term "fluidics device" and "fluidics system" as herein disclosed, but "fluidics device/system" can additionally or alternatively refer to devices on a larger scale that operate to route fluids from one location to another. In examples, fluidic devices/systems of the present disclosure can be automated.

Multiplexed Electronics: The term "multiplexed electronics" refers to electronics capable of multiplexing in which multiple analog or digital signals are combined into one signal over a shared medium. A "multiplexer" refers to a combinational logic circuit that acts as a switcher for multiple inputs to a single common output line. Also known as a "MUX", it delivers either digital or analog signals at a higher speed on a single line and in one shared device, but then recovers the separate signals at a receiving end.

Nanogap: The term "nanogap" refers to a pathway with nanoscale dimensions through which a biomolecule translocates in the process of traveling from a top chamber of a nanopore device as disclosed herein, to a bottom chamber (or vice versa). A nanogap is formed via a space between two transverse electrodes, and nanogap dimensions (e.g., width) can be modified by controlled electrochemical deposition, for example reversible pulse electrochemical deposition/dissolution. Herein, nanogap may also be referred to as "nanopore."

Nucleic acid: A deoxyribonucleotide or ribonucleotide polymer, which can include analogues of natural nucleotides that hybridize to nucleic acid molecules in a manner similar to naturally occurring nucleotides. In a particular example, a nucleic acid molecule is a single stranded (ss) DNA or RNA molecule, such as a probe or primer. In another particular example, a nucleic acid molecule is a double stranded (ds) nucleic acid, such as a target nucleic acid. The term "nucleotide" refers to a base-sugar-phosphate combination and includes ribonucleoside triphosphates ATP, UTP, CTG, GTP and deoxyribonucleoside triphosphates such as dATP, dCTP, dITP, dUTP, dGTP, dTTP, or derivatives thereof.

Optional: "Optional" or "optionally" means that the subsequently described event or circumstance can but need not occur, and that the description includes instances where said event or circumstance occurs and instances where it does not.

Protein: The terms "protein," "peptide," "polypeptide" refer, interchangeably, to a polymer of amino acids and/or amino acid analogs that are joined by peptide bonds or peptide bond mimetics. The twenty naturally-occurring amino acids and their single-letter and three-letter designations are as follows: Alanine A Ala; Cysteine C Cys; Aspartic Acid D Asp; Glutamic acid E Glu; Phenylalanine F Phe; Glycine G Gly; Histidine H His; Isoleucine Ile; Lysine K Lys; Leucine L Leu; Methionine M Met; Asparagine N Asn; Proline P Pro; Glutamine Q Gln; Arginine R Arg; Serine S Ser; Threonine T Thr; Valine V Val; Tryptophan W Trp; and Tyrosine Y Tyr. In one embodiment, a protein/peptide/polypeptide is an antibody or fragment or part thereof. In some embodiments, the protein/peptide/polypeptide may be post-translationally modified.

Raman Spectroscopy: A spectroscopic technique typically used to determine vibrational modes of molecules, although rotational and other low-frequency modes of systems may also be observed. Raman spectroscopy can be used in chemistry to provide a structural fingerprint by which molecules can be identified.

Sample: A mixture of molecules that comprises at least an analyte molecule that is subjected to manipulation in accordance with the nanodevices, chips, systems and/or methods of the disclosure.

Translocation: A change in location. As used herein, a translocation event refers to a biomolecule (e.g., DNA) moving through a nanogap.

Transparent substrate: A material made up of components with a uniform index of refraction. Transparent materials appear clear, with the overall appearance of one color, or any combination leading up to a brilliant spectrum of every color; light is allowed to pass through the substrate without appreciable scattering of light. The opposite property of translucency is opacity or non-transparent. Examples of transparent substrates include, but are not limited to, glass or quartz.

Under conditions sufficient to: A phrase that is used to describe any environment that permits the desired activity.

II. General Description

There are a number of challenges needed to be overcome in order to fully realize the potential of nanodevices integrated into chips. One issue with current approaches is that microfluidic interfaces with nanodevices occupy a large area of total chip size, which substantially reduces the density of nanodevices which can be included on a single chip. It can be very cumbersome and challenging to deliver different samples to different groups of nanodevices. For example, such delivery can require multiple layers of channels and this in turn can significantly reduce chip yield, as a result of the complexity of the overall assembly process. Of course, a reduction in the density of nanodevices reduces opportunity for high-throughput analysis. Yet another issue is that currently, a width of a barrier between adjacent microfluidic channels needs be large enough to compensate alignment error and overflow of adhesive structures, which can significantly increase etching time due to increased diffusion length. Accordingly, the travel distance to reach the tunneling junction may in turn be increased, which can lead to clogging and reduced detection rates.

It is herein recognized that the above-mentioned issues can be at least partially addressed via a nanodevice fabrication strategy that involves placing/fabricating cis- and trans-chambers around the tunneling junction structure (e.g., nanogap) in a manner that utilizes both sides of a substrate, in contrast to fabrication methodology that utilizes just one side of a substrate. By utilizing both sides of the substrate for the fabrication, the chambers placed/fabricated around the tunneling junction effectively correspond to a top chamber (cis-chamber), and a bottom chamber (trans-chamber), as opposed to the cis- and trans-chambers each being on a particular side (e.g., top) of a substrate. More specifically, in the fabrication approach outlined herein, the resultant top chamber is accessible (e.g., open) from a top of the nanodevice, but the bottom chamber is sealed at the top and hence is inaccessible from the top of the nanodevice. In turn, the bottom chamber is accessible (e.g., open) from a bottom of the nanodevice, but the top chamber is sealed at the bottom and hence is inaccessible from the bottom of the nanodevice.

The structure of nanodevices herein disclosed is advantageous in that density of nanodevices can be dramatically increased on one single chip (e.g., footprint of 10 µm×10 µm to 100 µm×100 µm, as compared to, for example, millimeter dimensions). Using the herein disclosed approach to nanodevice fabrication, nanodevices can be readily integrated in arrays on a single chip, and can be grouped into distinct groups. The structure design as herein disclosed enables integration of multiplexed electronics in the substrate, which may advantageously improve signal quality, and can enable simultaneous preparation of electrodeposition and sample analysis. Furthermore, the structure design of nanodevices as herein disclosed can simplify sample delivery. For example, a multiwell structure over the top, and optionally the bottom, surface may enable different samples to readily be provided to different groups of devices on a single chip, such that they may be analyzed in parallel, or sequentially, for example in a predefined sequence. This multiwell approach can reduce or avoid altogether issues such as leaking associated with microfluidic channels. Still further, via the structure design of nanodevices herein disclosed, the ionic current for each group of nanodevices on a single chip can capture translocation events from all of the nanodevices corresponding to a particular group, while the tunneling signals from individual nanodevices can be correlated to the total ionic current as groups. For example, for each group, ionic current corresponding to each nanodevice can be integrated to yield total ionic current associated with translocation events, and the tunneling signals from each nanodevice can be correlated to the integrated total ionic current. The integral of the ionic current can provide an indication of the total number of translocation events occurring in a particular group, which can reduce demand on electronics associated with the chips and nanodevices of the present disclosure.

Fabrication Procedures According to One or More Exemplary Embodiments

Figure 2A:
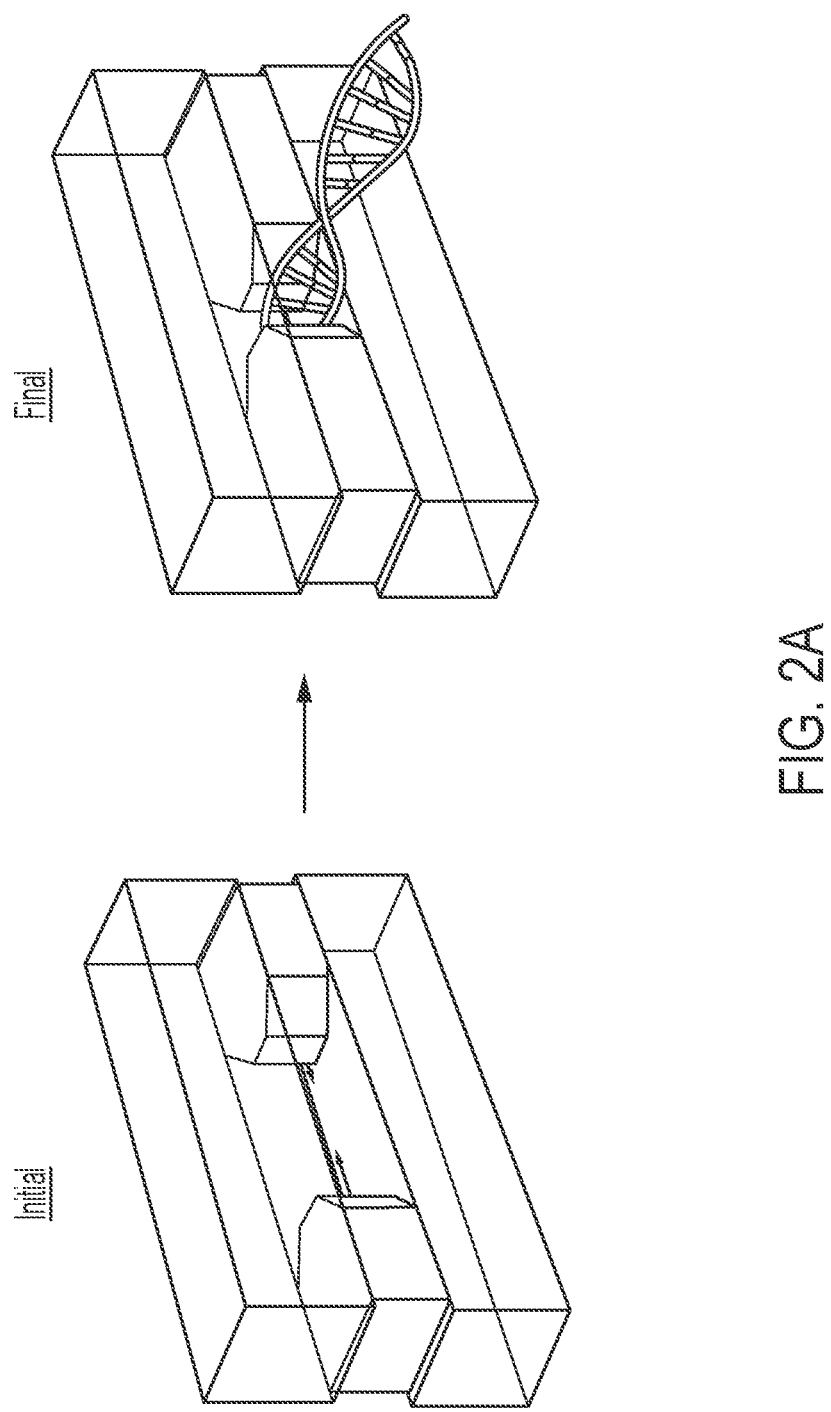
FIG. 2A illustrates a representative example of an initial structure (left) that serves as a starting point for fabrication of nanodevices of the present disclosure, and a final structure following narrowing of the gap between electrodes.

Example steps in the fabrication process of nanodevices of the present disclosure are now discussed with reference to FIG. 2A, and steps 1-8 of FIG. 2B. Turning to FIG. 2A, depicted on the left is an initial structure that serves as a starting point for nanodevices of the present disclosure, with a pair of electrodes sandwiched between dielectric passivation layers to form a confined cavity. The starting distance between the electrodes may be between 200 nm to 5 µm, for example between 500 nm to 2 µm, for example between 600 to 2 µm, for example about 1 µm. The thickness of the cavity may be about 10~20 nm, which can be readily prepared through top-down lithography protocols. Next, the gap between the electrodes can be finely reduced in a reversible and controllable way (e.g., controlled electrochemical deposition) to construct a tunneling junction, which simultaneously forms the nanopore device at the narrowest position (refer to image on the right at FIG. 2A). The electrodes and the dielectric layers separate the chip space into two chambers (e.g., top and bottom), with the nanopore and the tunneling junction self-aligned in between, such that any molecule translocating from one chamber to the other through the nanopore must pass between the electrodes.

Figure 2B:
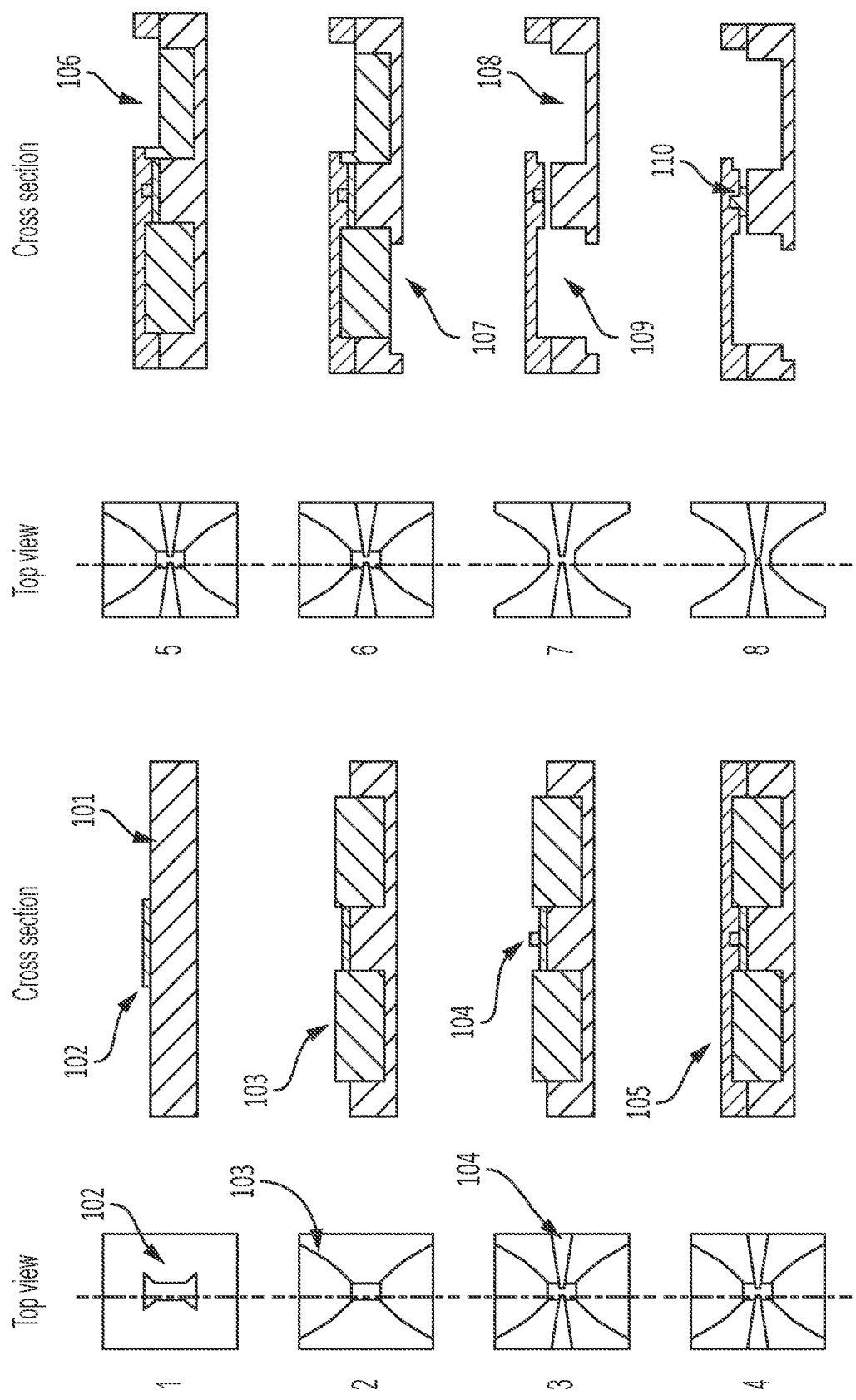
FIG. 2B shows schematics illustrating various stages of fabrication of a disclosed nanodevice in accordance with embodiments disclosed herein.

Turning now to FIG. 2B, steps 1-6 refer to example fabrication steps of the nanopore device including construction of the initial device (e.g., similar to that depicted at FIG. 2A), and steps 7-8 refer to the final preparation. Drawings at FIG. 2B are not to scale for clarity. The dotted lines associated with the top-view show the position of the cross-section.

Layout of Sacrificial Structures

The first step involves defining an inner sacrificial layer 102 on substrate 101. The substrate 101 may comprise one or more of silicon with $SiO_2$ and/or $Si_3N_4$ coating, sapphire, quartz, or other material compatible with top-down lithography. The inner sacrificial layer 102 may comprise one or more of chromium (Cr), nickel (Ni), magnesium (Mg), and/or aluminum (Al). A thickness of the inner sacrificial layer may be between 1-100 nm, with dimensions of 10 µm×10 µm.

The second step involves defining an outer trench and outer sacrificial layers 103 on both sides of the inner sacrificial layer with overlapping edges. With regard to the second step, etching of the trenches into the substrate 101 may be done via, for example, reactive-ion etching (RIE). The depth of the etching may be between about 100 and 500 nm. The trenches may be filled with one or more of Al, Mg, Cr, and/or Ni. A thickness of the metal corresponding to the outer sacrificial layers 103 may be at least somewhat thicker than the RIE etching depth. For example, thickness of the metal may be between 20-500 nm thicker, for example 20-200 nm thicker, for example, 200-300 nm thicker. As a result of this increased thickness, the metal corresponding to the outer sacrificial layers 103 is slightly higher than the original upper surface of the substrate 101. The outer sacrificial layers 103 may extend from 10-120 μm, for example between 20-100 μm, away from the center of the inner sacrificial layer 102.

Construction of Initial Electrodes and Fluidic Channels/Chambers

The third step involves defining transverse electrodes 104 at the center of inner sacrificial layer 102. The pair of transverse electrodes 104 may be fabricated with their tips aligned with the center of the inner sacrificial layer 102 and outer sacrificial layers 103. As mentioned above, the initial gap distance between electrodes may be between 200 nm to 5 μm, for example between 500 nm to 2 μm, for example between 600 nm to 2 μm, for example about 1 μm. The initial gap distance may be determined by resolution of photolithography. The pair of transverse electrodes 104 may be comprised of one or more of gold (Au), platinum (Pt), and/or palladium (Pd), or other metal or alloy, compatible with top-down lithography and subsequent electrochemical deposition. As used herein, the term "other metal" includes ruthenium (Ru), rhodium (Rh), palladium (Pd), osmium (Os), iridium (Ir), platinum (Pt), gold (Au), silver (Ag), copper (Cu), rhenium (Re). Thickness of the metal corresponding to the initial pair of transverse electrodes 104 may be between 20-100 nm.

The fourth step involves sealing the top of the electrodes by dielectric layer 105. Specifically, the whole upper (top) surface of the chip is fully passivated with $HfO_2$, $ZrO_2$, $SiO_2$, $Si_3N_4$, or combination of multiple layers of dielectrics. This may be done via atomic layer deposition (ALD), or plasma enhanced chemical vapor deposition (PECVD). In some examples, an additional one or more layers of SU-8 polymer (or parylene or other polymer dielectrics) can optionally be applied to assist in sealing. Thickness of the dielectric layer 105 may be between about 100 nm to about 100 μm. In some examples, before the ALD or PECVD coating process, a 0.5-2 nm Cr or Ti or other metals are sputtered over the electrodes surface, optionally treated by oxygen plasma, to promote better adhesion and sealing of the dielectric layer deposited by the ALD or PECVD on the electrodes and substrate, especially in the region of the side edges of the electrodes.

The fifth and sixth steps involve using a masked RIE process to selectively open first window 106 and second window 107 to expose outer sacrificial layer 103 from the top side of the device (window 106), and from the bottom side of the device (window 107). Thus, window 106 is produced by etching of dielectric layer 105 from the top side of the device, whereas window 107 is produced by etching of substrate 101 from the bottom side of the device.

Once steps 1-6 have been carried out, the initial device may be stored at ambient environment for later use.

Preparation of Nanopore and Tunneling Gap Before Recording

The initial devices have to be prepared with appropriate dimensions just prior to being used for recording. Accordingly, step 7 involves removal of each of the inner (102) and outer (103) sacrificial layers by wet chemical etching, to yield top chamber 108 and bottom chamber 109 on both sides of the nanoscale channel created at the center. The size of the top chamber 108 and bottom chamber 109 may be between 1-100 μm in diameter. In an embodiment, the sacrificial layers are first removed to construct a continuous space by properly feeding a first etchant (e.g., Al etchant) and then a second etchant (e.g., Cr etchant) through the fluidic channels, such that a central nanoscale cavity around the electrodes 104 is formed, with the nanofluidic channels on both sides connected to the top (108) and bottom (109) chambers. Phosphate buffer (PB) containing 5 mM $KH_2PO_4$ and 5 mM $NaHPO_4$ (pH 7.26) may be used to flush the channels before and after each etching step, and the ionic conductance between the chambers may be measured. Typical conductance before the final chemical etching is finished may be below about 20-30 pS as determined by the baseline of the electronics, and about 2-5 nS after the inner sacrificial layer 102 is fully removed.

Next, step S involves using feedback control techniques adopted from previous studies (Wang, Y., Sadar, J., Tsao, C. W., Mukherjee, S., Qing, Q. "Nanopore chip with self-aligned transverse tunneling junction for DNA detection." Biosens Bioelectron 2021, 193: 113552; Sadar, J.; Wang, Y.; Qing, Q., Confined Electrochemical Deposition in Sub-15 nm Space for Preparing Nanogap Electrodes. ECS Trans 2017, 77 (7), 65-72; Qing, Q.; Chen, F.; Li, P.; Tang, W.; Wu, Z.; Liu, Z., Finely tuning metallic nanogap size with electrodeposition by utilizing high frequency impedance in feedback. *Angew Chem Int Ed Engl* 2005, 44 (47), 7771-5), which are hereby incorporated by reference in their entirety, the channels are filled with electrolyte containing a metal (e.g., Au, Pt, Pd, Ni, Co, or other metals compatible with the electrochemical deposition process), and the conductance between the transverse electrodes is monitored in real time to control electrochemical deposition of metal onto the existing electrodes 104. In one example, the electrolyte is comprised of 18.5 mM $KAu(CN)_2$ and 180 mM potassium citrate, and the conductance between the transverse electrodes is monitored in real time to control electrochemical deposition of Au onto the existing electrodes 104 with Ag/AgCl serving as the counter electrode. In examples, the final dimension of the nanopore and the tunneling junction 110 can be finely and reproducibly tuned with a reversible pulsed deposition strategy as explained below. Thickness of the final electrode cap may be defined by the thickness of the original inner sacrificial layer 102. It may be understood that the feedback controlled electrochemical deposition process within the confined cavity created by the etching of the inner sacrificial layer 102 closes the initial gap between electrodes 104, thereby forming the nanopore and transverse tunneling junction 110 simultaneously. In embodiments, the gap between electrodes may be between about 1 nm and 100 nm, between about 10-50 nm, between about 1-20 nm, between about 20-60 nm, including, but not limited to between 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 nm. In embodiments, the smallest size of the gap is comparable to the diameter of a single biopolymer. For example, the diameter of a single strand DNA molecule is about 1.0 nm. In embodiments, the largest size of the gap is comparable to the diameter of the diameter of the three-dimensional size of a molecule, such as a protein molecule, that is to be characterized, such as on the order of about 5 nm to 10 nm, with larger ones close to 100 nm.

Figure 3C:
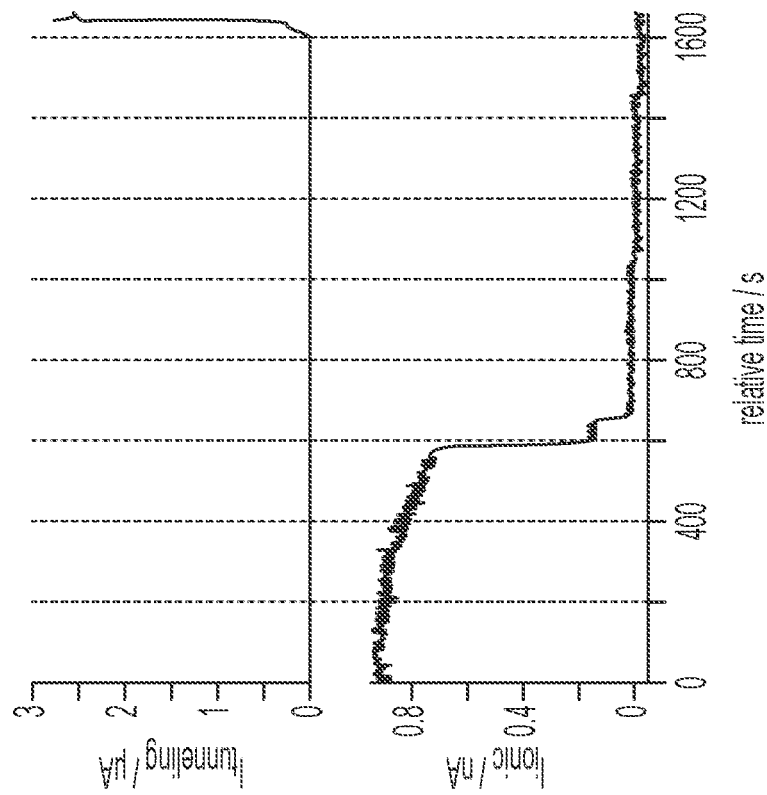
FIGS. 3A-3E illustrate how reversible pulsed electrochemical deposition can be used to precisely control nanopore and tunneling junction dimensions.
Figure 3A:
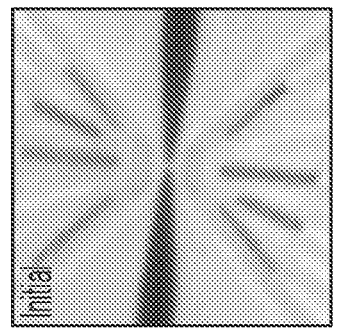
Figure 3B:
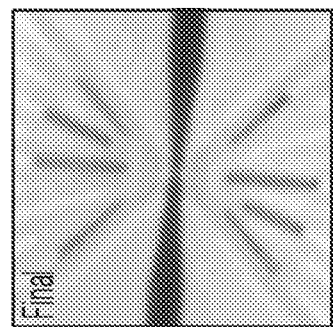

FIGS. 3A-3D depict reversible pulsed electrochemical deposition to precisely control the dimension of nanopore and tunneling junction. FIGS. 3A-3B illustrate optical images of an initial device (FIG. 3A) and the final tunneling junction (FIG. 3B). FIGS. 3A-3B show optical images from the backside of the cover slips of the initial transverse electrodes (FIG. 3A), and after the electrochemical deposition where the gap is closed under precise control (FIG. 3B). As the electrochemical deposition progresses, one may typically observe first a drop in the ionic conductance between the top and bottom chambers, then later an increase in the conductance between the transverse electrodes signaling a short (FIG. 3C). Specifically, FIG. 3C illustrates during a deposition as the electrodes become shortened, simultaneously recorded traces of currents between top and bottom chambers ($I_{ionic}$) under a bias of 50 mV and between transverse electrodes ($I_{tunneling}$) under a bias of 1.45 mV. It is herein recognized that if a constant deposition bias is applied, there will be significant side growth on the electrodes and it may take a very long time to short the electrodes. Without being bound to a theory, this is attributed to the quick exhaustion of metal ions (e.g., $Au(CN)_2^-$) near the tips of the electrodes in the confined nanoscale cavity. The deposition mostly happens on the outer edges of the electrode where the access to external ion supply is easier. Therefore, a pulsed deposition strategy can be utilized to make the deposition at the tips more effective to close the gap. Namely, deposition potential can be applied for a short period of time, and then the system was left to rest at a potential (the "rest" potential) where no Redox reaction is happening such that the ion concentration inside the central cavity can restore by diffusion. There is a clear correlation between the side growth on the electrodes and the width of the deposition pulses (FIGS. 4A-4B). A systematic comparison identified the optimal pulse width for effective tip growth to be 2~50 ms with a rest potential period of ~2 s.

Turning briefly to FIGS. 4A-4B, depicted are specific frames of time lapse recording during the metal depositions with different deposition pulses. FIG. 4A shows the tip shape before and after the deposition with a 400 ms, 950 mV square wave followed by a 1.6 s, 0 V resting potential. FIG. 4B shows the tip shape with a 2 ms, 950 mV square wave followed by a 1.998 s, 500 mV resting potential. The scale bar is 20 µm. With a short deposition pulse width of 950 mV and higher resting potential, the final deposition tip shows less side growth and forms quantum contact in a shorter period of time.

Figure 3E:
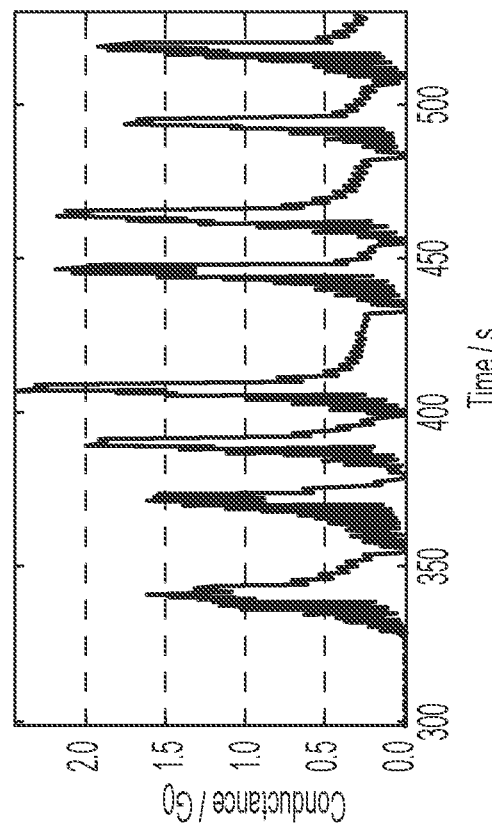
Figure 3D:
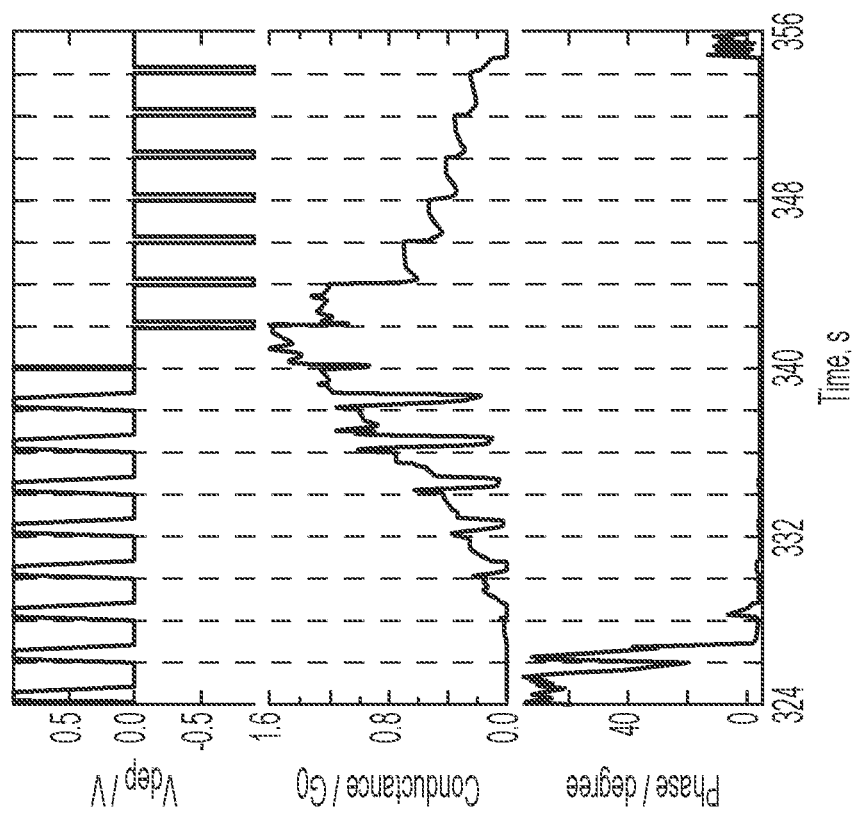
Figure 4D:
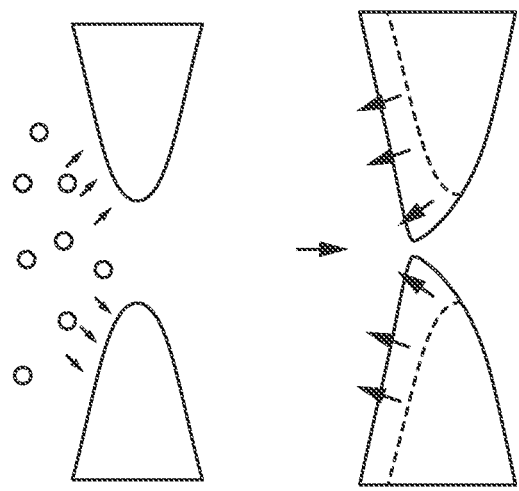
FIGS. 4C-4D illustratively depict options for influencing/optimizing nanopore geometry during the process of electrodeposition of metal onto tunneling junction electrodes.

A unique advantage of using electrochemistry to tune the tunneling junction is that this process is fully reversible. A control program was created which can actively track the conductance across the transverse electrodes at the end of every period of the pulsatile deposition. If the conductance is above a threshold, the program will flip the polarity of the bias $V_{dep}$ to switch from the deposition mode to dissolution mode such that metal (e.g., Au) is removed in controlled steps. FIG. 3D gives such an example where the transition happened at 342 s when the conductance reached above 1 conductance quantum $G_0$. More specifically, FIG. 3D depicts a record of the potential $V_{dep}$ applied to Ag/AgCl counter electrodes for controlled metal (e.g., Au) deposition (when $V_{dep}>0$) and dissolution (when $V_{dep}<0$), and the corresponding amplitude (in units of conductance quantum $G_0=2 \cdot e^2/h=77.5$ µS) and phase of the AC conductance between the transverse electrodes recorded at 10.13 kHz. An automated control program monitors the conductance during the deposition. When the conductance reaches a threshold above 1 $G_0$, the program switches the polarity of $V_{dep}$ (at 342 sec) to remove metal (e.g., Au) from the electrode with negative pulses.

$G_0$ was used as the typical threshold as it can serve as the calibration of zero distance between the electrodes as they make first atomic contact. Such process can be repeated with high reproducibility to open and close the tunneling gap and generate a stable junction as defined by the final tunneling conductance (FIG. 3E). Specifically, FIG. 3E depicts conductance between transverse electrodes showing controlled reversible closing and opening of the gap for multiple times.

It is herein noted that as the feedback control signal, the conductance between the transverse electrodes may be tracked using an AC signal ranging from 1 Hz to ~10 kHz with a lock-in amplifier. For example, when higher frequency is used, the conductance may start showing clear changes at longer distance on the order of tens of nm due to the capacitive component, which gives wider range of control in distance. This is also demonstrated in the recorded phase of the AC conductance in FIG. 3D when 10.13 KHz reference signal was used, which showed an early transition in phase from more capacitive to more resistive before significant changes in the amplitude happened later. Nevertheless, in this disclosure, dimensions are focused on that should best fit the diameter of the DNA molecules, therefore, low frequency AC signals (5 Hz) were used to monitor and control the junction's size which is most sensitive in the tunneling region. For devices used in DNA translocation devices, the disclosed control program can be used to stabilize the junction conductance to a predetermined setpoint, for example, ~1 nS, corresponding to a gap distance of about between 3-4 nm, for example about 3.4 nm. In one embodiment, a DC bias can be used to monitor the conductance and control the nanogap size which is most sensitive within the tunneling region of ~1 nm.

Thus, construction of nanopore devices of the present disclosure via the use of feedback-controlled electrodeposition of metal onto a pair of initial electrodes sandwiched between two dielectric passivation layers, can be used to shrink an initial gap/cavity such that a nanopore device and a tunneling junction are formed simultaneously and in a self-aligned manner. The nanogap of the nanodevice may be self-aligned, which refers to how the nanogap is fabricated utilizing electrodeposition of the metal onto the the pair of initial electrodes between the two dielectric passivation layers. As used herein, a "self-aligned" nanogap is one fabricated by a process that causes the nanogap to be formed at a point, along the length of the fluidic channel, at which the electrodes contact the fluid. It is herein recognized that in some examples, due to quick depletion of metal ions in the confined space, the size and sharpness of tunneling electrodes can degrade (e.g., become blunt) over some period of time. It is herein recognized that during the feedback-controlled electrodeposition of metal onto the pair of initial electrodes, metal deposition can tend to happen more on the edges of the electrodes which have better access to the metal ions than the tip region where depletion happens much quicker. In addition, due to the preferential deposition of metal on the edges of the electrodes, overall deposition time can be quite long before the tunneling junction reaches desired size (e.g., on the order of 1 to several nanometers or thereabouts).

Accordingly, disclosed herein are several approaches that improve various aspects of the nanopore device construction procedure. Specifically, herein disclosed is methodology that may improve at least 1) deposition speed for the final device, 2) tip sharpness corresponding to the electrodes comprising the tunneling junction, and 3) stability of the finally formed junction.

In one example, fast pulsed electrodeposition was compared to slow pulse or continuous deposition methodology. In a typical experiment, it was found that the optimal deposition time is <50 ms during which the electrodes are held at a reducing potential to allow metal ions to be reduced and deposited onto the electrode, followed by a 500 ms to about 2 second (2000 ms) rest time. During the rest time, the electrodes are held at a potential where no Faradaic current is present to allow a diffusion process to compensate the consumed metal ions near the tips of the electrodes. It has been found with the current setup that 2 ms-5 ms (e.g., 2 ms, 3 ms, 4 ms, 5 ms) can be an optimal deposition time. However, shorter deposition times may also be used without departing from the scope of this disclosure. For example, where equipment bandwidth allows, shorter deposition times including deposition times between 10 µs and 1 ms may be used. More specifically, deposition times may be between 10-500 µs, or 500 µs–1 s, or 10-450 µs, or 10-400 µs, or 10-350 µs, or 10-300 µs, or 10-250 µs, or 10-200 µs, or 10-150 µs, or 10-100 µs, or 10-90 µs, or 10-80 µs, or 10-70 µs, or 10-60 µs, or 10-50 µs, or 10-40 µs, or 10-30 µs, or 10-20 µs. In some examples, deposition times could be even lower, such as below 10 µs, for example below 1 µs. It is herein recognized that shorter deposition times may in turn enable shorter rest times, thereby improving (e.g., reducing) an overall timeframe for construction of the nanodevices of the present disclosure.

In another example, it is herein disclosed that a small bias of about 50-100 mV between the two chambers (e.g., cis and trans) can encourage electrophoresis and electroosmotic flow between the chambers without affecting the Faraday process at the electrodes. This can have the effect of forcing a faster compensation of metal ions into the deposition region, which may enable shorter rest times and thus shorter device construction times, similar to that discussed above.

Figure 4C:
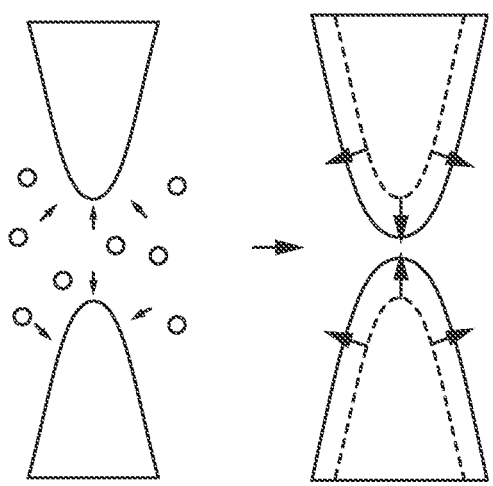

In another example, it is herein recognized that an asymmetric setup may lead to asymmetric deposition, which may in turn result in a sharper tip corresponding to each of the tunneling electrodes. Turning to FIG. 4C, depicted is an example illustration showing that when metal ions (depicted as spheres) are allowed to uniformly diffuse to the electrodes, the overall radius of the electrodes will increase. Specifically, with regard to FIG. 4C, dashed lines indicate shape of the electrodes pre-uniform deposition process, whereas the arrows indicate how the electrodes increase in size uniformly as a result of the uniform deposition process. Alternatively, turning to FIG. 4D, if metal ions (depicted as spheres) are provided in just one of the two chambers, asymmetric deposition may enable a sharper electrode shape near the tip, as indicated at the bottom-half of FIG. 4D.

It is further recognized herein that a newly prepared tunneling junction that has reached a desired distance as indicated by the conductance between the electrodes may be unstable over a period of time. A solution to this may be to utilize the reversibility of the electrochemical process to repeatedly construct the gap any number of times. Namely, a method may include expanding the junction by metal oxidation (by switching the polarity of potential applied at the metal electrodes) so that freshly deposited metal is removed, followed by a redeposition step to reach the desired gap size again. The purpose of this oxidation and reducing cycle may be to fill in the most active sites on the electrodes (e.g., sites that are most likely to deform/reshape under ambient conditions over time), and remove atoms that are most active and mobile in the reverse process. By repeating this process any number of times (e.g., 10-1000×), surface sites that are most likely to cause reshaping that leads to unstable gap geometry may be sacrificed, resulting in a "retarded" surface and hence a stable gap.

Operation of the Nanodevices According to Embodiments

Figure 5B:
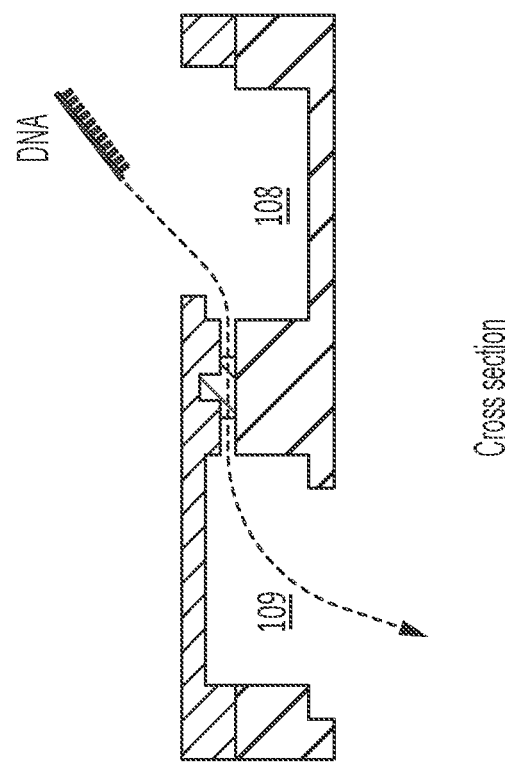
FIGS. 5A-5B depict a top view (FIG. 5A) and cross sectional view (FIG. 5B) of a nanodevice in accordance with embodiments disclosed herein, illustratively depicting a DNA translocation path through a nanogap.
Figure 5A:
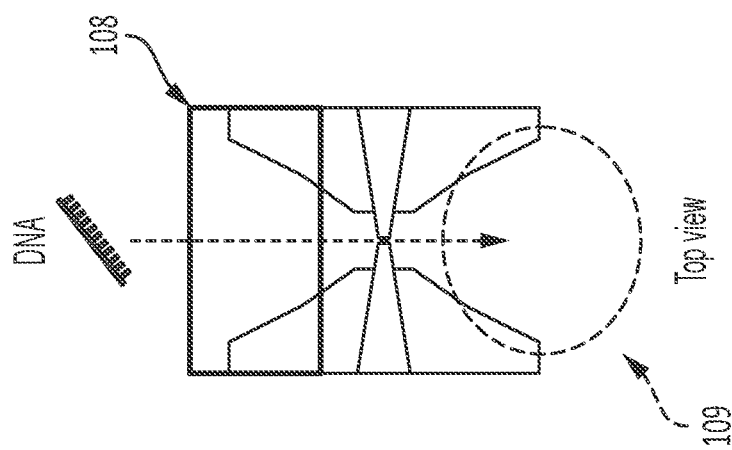

Turning now to FIGS. 5A-5B, depicted is a top view (FIG. 5A) and cross-sectional view (FIG. 5B) of a nanodevice fabricated according to embodiments herein disclosed, illustrating how a biomolecule (DNA in this case) moves through the nanodevice. In an embodiment, the molecule can be delivered to the top chamber 108, and it may move under driving bias applied between top chamber 108 and bottom chamber 109 to pass the tunneling junction/nanopore at the center and exit from the bottom chamber 109. The ionic current between the top chamber 108 and bottom chamber 109 and the tunneling current between transverse electrodes can be used to analyze the biomolecule. In other examples, the movement of the biomolecules can be reversed by changing the polarity of the potentials applied between the top and bottom chambers, such that the same biomolecules can be controlled to pass the tunneling junction/nanopore multiple times in different directions for repeated analysis.

Also within the scope of this disclosure is the use of optical signals in addition to or alternatively to reliance on one or more of ionic current and tunneling current to analyze a biomolecule. For example, in embodiments, a nanodevice of the present disclosure can be mounted on a microscope where the objective lens can focus on the nanogap through a transparent substrate or from the top side of a non-transparent substrate, for tracking the motion and translocation of molecules inside the nanogap with fluorescence signals. The lens can additionally or alternatively be used for detecting Raman signals from the gap as the molecules passes through the electrodes (for example via Raman microscopy techniques). The electrodes will be connected to a voltage source and an electrometer to record the tunneling signal across the gap. Between the top and bottom chamber, two electrodes can be used to apply a bias potential of 10-1000 mV for driving the molecule through the gap.

In embodiments, as a molecule analyte is delivered to the top chamber on one side of the nanogap, the molecule may be guided through the nanogap by a bias, such as between 10-1000 mV, applied between the top and bottom chamber. It is contemplated that the bias magnitude can be tuned to satisfy desired speed of translocation. In some embodiments, it may be advantageous to mount, at least for some predetermined amount of time, the molecule to the metal electrodes, including but not limited to (1) simple blocking by sizes of the molecule in relation to nanogap dimensions, (2) modifying the molecule to have binding sites that can form chemical bonds to the metal such as, for example, thiol groups that can bind to gold surface, (3) modify the surface of the metal electrodes so that they will have specific binding sites that will recognize specific functional groups on the molecule at the ends, or along the sides of the molecules. The binding site in these configurations can be valence chemical bonds, such as the S-Au/Pt/Pd between sulfhydryl group and the metal such as Au, Pt and Pd when they get in contact. For example, the lysines in protein molecule can be modified by thiolation reagents to produce free sulfhydrl groups which forms valence chemical bonds with the metal surface. The binding site can also be designed to be specific high-infinity interactions between proteins and functional groups, such as the avidin-biotin interaction. For example, on the substrate thiolated biotin may be included to modify the metal surface through the S-Au/Pt/Pd bond, exposing biotin group into the medium. The protein molecule can be then linked with streptavidin will bind to the biotin groups when it comes to the nanogap. Other interactions such as hydrogen bonds, π-π interactions, etc., can also be used.

It is contemplated that a mounting event can be detected both by the ionic current between the top and bottom chambers and the tunneling current between the metal electrodes, and the conductance of the molecule can be evaluated when such event is detected. In addition, optical characterization such as tip-enhanced Raman spectrum (TERS) can be performed through the transparent substrate or from the top side of a non-transparent substrate to understand the dynamic structure of the molecule.

In some embodiments, the present disclosure provides a method for sampling/characterizing molecules, small particles or small samples of material which comprises delivering a sample, such as a molecule analyte, into the top chamber on one side of the nanogap and guiding the sample, such that molecule analyte travels through the nanogap by a bias, such as a bias between about 1 and about 1000 mV, applied between the top and bottom chamber.

In some embodiments, the present disclosure presents a measurement device for analyzing samples consisting of single molecules, small particles, or small quantities of matter. The molecular measurement device includes at least one nanofluidic channel through which a solution containing a sample to be analyzed can flow, and a pair of electrodes defining a nanogap across the nanofluidic channel through which the sample is passed. In embodiments, the size of the nanogap is selected based on the molecular size of the matter samples to be observed with the apparatus, and as such, permits only a single matter sample to pass through the nanogap at a time. In embodiments, the distance between electrodes gets in the 1-100 nm range to form a self-aligned nanogap with the narrowest bottleneck in the path between the two said channels/chambers. It is contemplated that the nanogap can be tuned during the electrochemical deposition process to address different properties for molecules of different size and geometry. In embodiments, the sample includes DNA, such as single stranded DNA and/or double stranded DNA. In embodiments, the sample includes RNA. In embodiments, the sample includes protein. Other embodiments include small molecules, any number of various polymers, and the like.

The nanogap provides an output representative of an environmental condition within the nanogap which changes in response to the presence of a sample within the nanogap. These environmental characteristics may be electrical or optical.

In further embodiments, the present disclosure provides a method to measure the conductance and optical properties such as tip-enhanced Raman spectrum from single molecules by detecting the individual mounting event of single molecules by the correlated ionic current between the said channels/chambers and the tunneling current between the said metal electrodes (e.g., through the defined nanogap), and then perform the electrical and/or optical characterization.

Figure 6A:
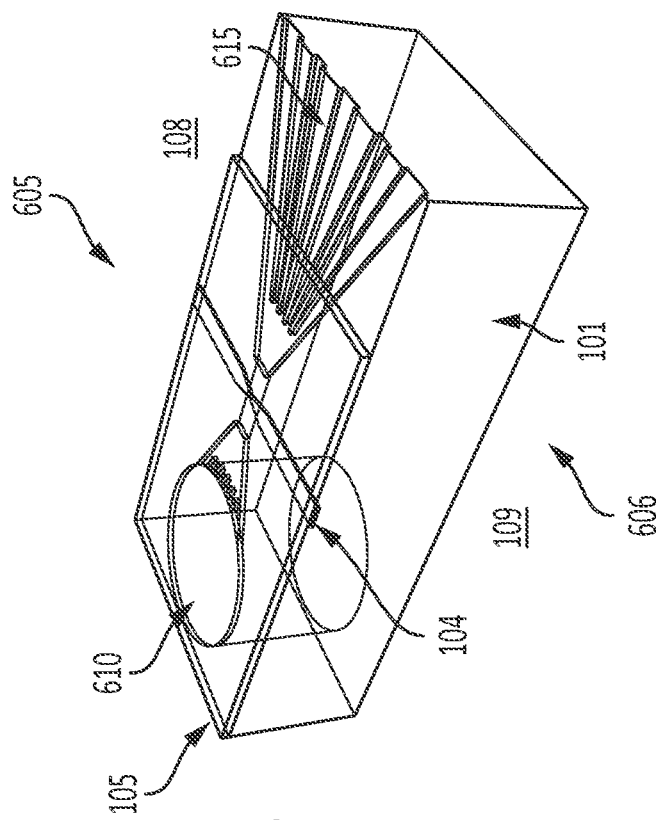
FIGS. 6A-6B depict three-dimensional illustrations of a nanodevice in accordance with embodiments disclosed herein.
Figure 6B:
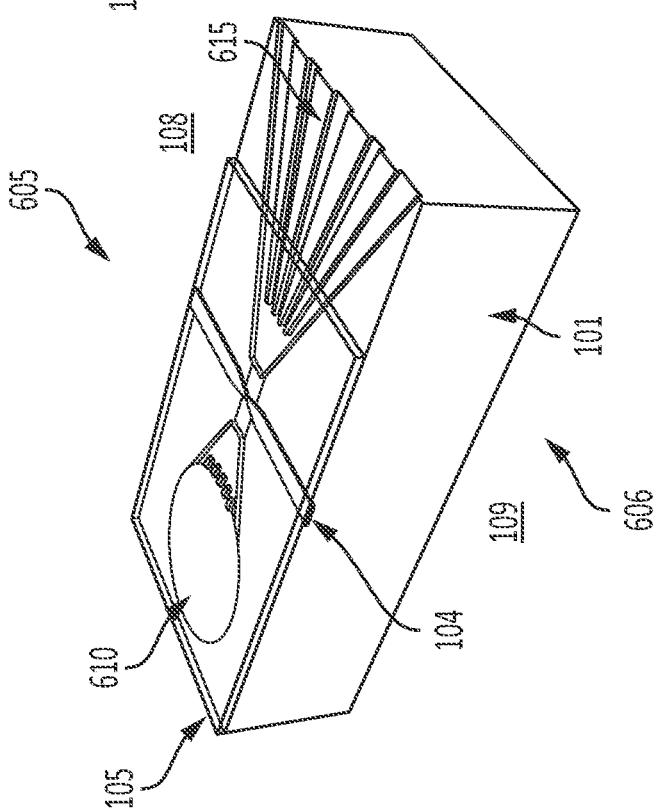

Turning now to FIG. 6A-6B, depicted are two three-dimensional illustrations of portions of nanodevices of the present disclosure. FIG. 6A is depicted as non-transparent, whereas FIG. 6B is depicted as transparent to show a view of the interior of a portion of such a nanodevice. With regard to the portions of the nanodevices shown at FIGS. 6A-6B, the nanodevice is oriented with a top 605 and bottom 606. Also depicted is substrate 101, transverse electrodes 104, and dielectric layer 105, and the general vicinity of the top chamber 108 and bottom chamber 109. Further depicted is through-hole 610 and grooves 615. Grooves 615 in the trenches are built to guide the analyte in the top chamber 108 to pass through the sealed portion (e.g., sealed at the top and bottom) of the nanodevice structure by way of the nanogap positioned between the transverse electrodes 104, en route to the through-hole 610 to the bottom chamber 109.

As discussed above, an advantage of fabricating nanodevices as herein disclosed with a top chamber and a bottom chamber, is that the design enables a significant reduction in the area that the microfluidic interface occupies on one side (e.g., top) of the devices. Accordingly, by using the fabrication methodology disclosed herein, density of the nanodevices on a single chip may be increased substantially as opposed to, similar designs where the microfluidic interface corresponding to cis- and trans-chambers is associated with just one side (e.g., top) of a nanodevice.

Hence, via the fabrication methodology herein disclosed, large numbers of nanodevices may be incorporated into a single chip. As representative examples, a single chip may correspond to a starting substrate that is a 170 um thick 1-inch quartz coverslip (Electron Microscopy Sciences, Item #: 72256-02), a 500-μm thick 4-inch quartz wafer (University wafer, Item #: 518), or a single crystal silicon wafer, or other similar such starting substrate. In such examples, thousands (e.g., greater than 1000, tens of thousands or more, and any number therebetween) may be incorporated into a single chip. It is within the scope of this disclosure that predetermined numbers of nanodevices (e.g., tens, hundreds, or even thousands) can be grouped into distinct regions of such a chip, to enable delivery of various sample to different groups at the same time.

Figure 7:
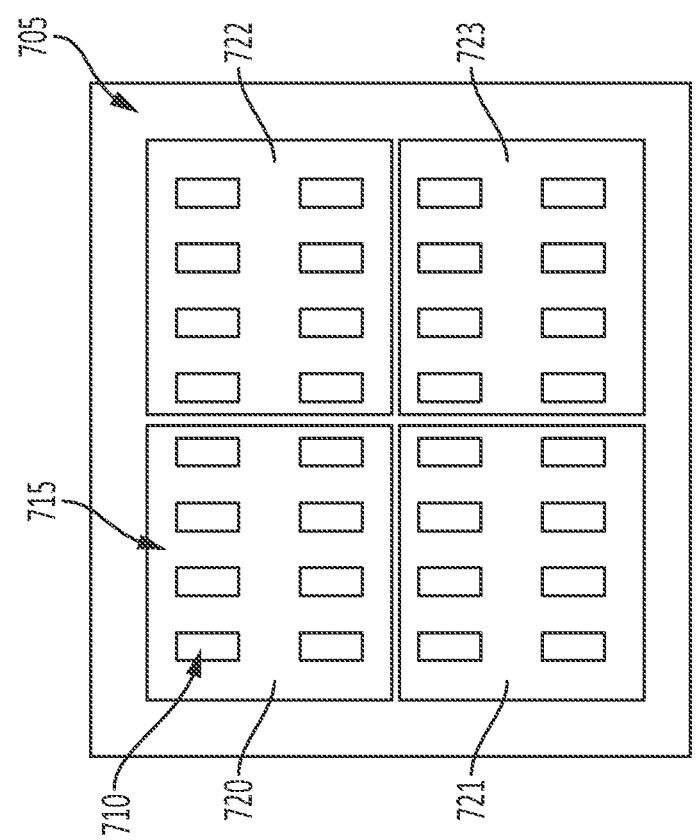
FIG. 7 schematically illustrates a single chip containing a plurality of nanodevices in accordance with embodiments herein disclosed, the plurality of nanodevices arranged in arrays of defined groups.

Turning to FIG. 7, depicted is a single chip 705, with a plurality of different nanodevices 710 integrated into the single chip 705. Further depicted is a plurality of different groups 715 of nanodevices 710. In this example illustration, each group 715 includes eight nanodevices, but as discussed above it is within the scope of this disclosure that each group 715 include tens, hundreds, or in some examples even thousands of individual nanodevices 710. Furthermore, just four groups 715 are shown, specifically first group 720, second group 721, third group 722, and fourth group 723. However, it is within the scope of this disclosure that there may be tens of groups, hundreds of groups, or in some examples even thousands of different groups. A footprint of one nanodevice 710 may be on the order of 10 μm×10 μm up to about 100 μm×100 μm.

Thus, fabricating the nanodevices as disclosed herein with a top chamber (e.g., top chamber 108) and a bottom chamber (e.g., bottom chamber 109) enables the incorporation of a large number of nanodevices into a single chip, and further enables the grouping of a plurality of nanodevices into individual groups. This, in turn, can significantly reduce complexity associated with sample delivery to nanodevices and groups of nanodevices. For example, a multiwell structure positioned over the top and bottom surface of chips including nanodevices of the present disclosure can be used to readily deliver samples to different groups of devices. Furthermore, multiplexed electronics can be integrated into the substrate (e.g., substrate 101), which can improve signal quality and enable simultaneous preparation of electrodeposition and sample analysis.

As one example, as discussed above for a pulsed electrochemical deposition process, there is a brief pulse followed by a resting period. It is herein recognized that for a chip 705 such as that illustrated at FIG. 7 with a plurality of nanodevices 710 in groups 715, multiplexed electronics may be used to sequentially conduct pulsed electrochemical deposition operations for all or a select number of nanodevices of the chip. For example, a pulse may be provided to a first nanodevice, then a second nanodevice, then a third nanodevice, then a fourth nanodevice, and so on down the line for however many nanodevices the pulsed deposition operation is desired. Because the pulse is of such a short duration (e.g., 2-5 ms or even lower, such as in the µs range) compared to the rest period (e.g., 500 ms to 2 seconds), a large number (e.g., an entirety) of nanodevices on a chip may be sequentially pulsed followed by a rest period, such that by the time all of the nanodevices have been pulsed, the process can be repeated again. In other words, via the sequential pulsing of nanodevices, each nanodevice can be pulsed within a time span equal to or less than a time frame of the rest period for the initial nanodevice that is pulsed. The sequential nature of the pulsing/rest sequence can be controlled electronically as a function of each of pulse time, rest time, and number of nanodevices for which pulsed electrochemical deposition is desired, to optimize electronics resources, save time for preparing chips of the present disclosure, and improve upon reproducibility for nanodevice fabrication. It is also within the scope of this disclosure that certain nanodevices and groups of nanodevices can be undergoing a pulsed electrochemical deposition operation while other nanodevices/other groups of nanodevices are provided samples for analysis thereof.

Figure 8:
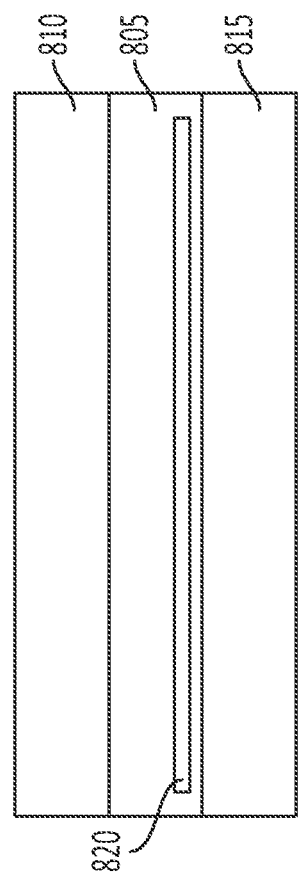
FIG. 8 depicts a high-level illustration of a single chip of the present disclosure, in association with a top multiwell structure, a bottom multiwell structure, and with multiplexed electronics integrated into the substrate of the chip.
Figure 8:

Turning to FIG. 8, a high-level schematic illustration of a chip 805 in conjunction with a top multiwell structure 810 and a bottom multiwell structure 815, is shown. For reference, arrow 801 points in the direction of a top of the chip 805, and hence, points in the general direction of the top chamber (not shown at FIG. 8). Alternatively, arrow 802 points in the direction of the bottom of the chip 805, and hence, points in the general direction of the bottom chamber (not shown at FIG. 8). While not explicitly illustrated, it may be understood that chip 805 includes a plurality of different groups of nanodevices.

The top multiwell structure 810 sits atop the top of chip 805, and while not explicitly illustrated, may be understood to comprise a plurality of wells. In examples, the number of wells corresponds to the number of groups of nanodevices. Similarly, the bottom multiwell structure 815 contacts the bottom of chip 805, and the number of wells associated with the bottom multiwell structure 815 may too correspond to the number of groups of nanodevices integrated into chip 805. Thus, in examples, top multiwell structure 810 and bottom multiwell structure 815 may include a same number of wells. However, in some examples, the top and/or bottom multiwell structures may have a different number of wells than the number of groups of nanodevices, without departing from the scope of this disclosure. In some examples, the bottom structure may not include individual wells, but instead may comprise one larger area. In this way, contacting a sample to a group of nanodevices integrated into chip 805 may include providing the sample to the appropriate well corresponding to a group of nanodevices for which the sample is intended to contact. Different groups of nanodevices can thus readily be contacted with different samples, for parallel analysis of various samples.

For example, it is within the scope of this disclosure that samples be provided via a multi-channel pipette, introduced manually or robotically and/or microfluidically. The samples may be introduced into the appropriate wells of the top multiwell structure 810, where the analytes present in the samples are then driven by a bias to translocate the nanodevices in each corresponding group. Following their translocation from the top chamber (e.g., top chamber 108) to the bottom chamber (e.g., bottom chamber 109), the analytes ultimately end up in the bottom multiwell structure 815. It is within the scope of this disclosure that, in some examples, the samples in the bottom multiwell structure 815 may be re-analyzed in similar fashion, may be analyzed in some other way to gain further information about the analytes in the analyzed samples, or may be stored for potential future use. Alternatively, the analyzed samples may be discarded.

The substrate (e.g., substrate 101) of the chip 805 may in some embodiments include integrated multiplexed electronics 820, as mentioned above. In an example, the multiplexed electronics include one or more of the following components: (1) a module that can change and hold the potential of an individual device (e.g., the potentiostat), (2) a module that can detect the tunneling current between an individual tunneling junction (e.g., a transimpedance amplifier), (3) a module that can send target potential to a selected device, and read tunneling junction signals from a selected device at specific time (e.g., a reader/writer), (4) a module that can switch the connection between the reader/writer and individual devices in programmable timing and sequence (e.g., the multiplexer), (5) a module that can translate digital and analog signals between external control electronics and the multiplexer such that individual devices can be addressed, and target potential can be delivered to specified devices, and tunneling current can be read from specified devices. These information can be controlled by an external controller and program to regulate the deposition process, and to collect tunneling current from all devices in a multiplexed way. In some embodiments, any electronic component utilized to interact with (e.g., to control or receive information from) at least one nanodevice may be integrated with in the chip 805 (e.g., fabricated on the substrate of the chip 805). Any or all of the electronic components and the multiplexed electronics that are integrated with the chip 805 may be fabricated on or in the chip 805 (e.g., on or in the substrate of the chip 805) before or after at least one (e.g., all) of the nanodevices have been fabricated.

Turning now to FIG. 9, depicted is an example system 900 of the present disclosure. System 900 may be part of a control system 14. The control system 14 is an interconnection of components forming a system configuration that provides a desired process response. In this embodiment, the control system 14 comprises a controller 12 that provides the logic and control instructions for the process, one or more sensors 18 that measure various physical properties, and one or more actuators 21 that change the state of the environment. The control system 14 may also include signaling means (not shown) that converts measurements from the sensor(s) 18 and/or instructions generated by the controller 12 into one or more signals that are then sent to other elements/components of the system. For example, the controller 12 may receive input data from the one or more sensors 18, process the input data, and trigger the actuators 21 in response to the processed input data based on instructions or code programmed therein corresponding to one or more routines, procedures, functions, methods, etc. The control system 14 may operate according to an open-loop system, closed-loop system, sequence control system, and/or a batch control system.

The controller 12 may comprise circuitry including, for example, one or more central processing units (CPU) including one or more processor cores, graphics processing units (GPU), programmable logic controllers (PLC), microprocessors, digital signal processors (DSP), one or more field-programmable gate arrays (FPGA), Application Specific Integrated Circuits (ASIC), or any suitable combination thereof. In some embodiments, the FPGA is utilized to provide real-time control of movement of a molecule or protein through the nanogap. For example, the FPGA may be utilized to move the molecule or protein back and forth through the nanogap one or more times. The circuitry of controller 12 may be coupled with or may include memory/storage devices and may be configured to execute instructions stored in the memory/storage to enable various applications, logic, etc., to run on the controller 12 and/or other elements of control system 14. In some embodiments, the controller 12 circuitry may be a special-purpose processor/controller to operate according to the various embodiments herein.

The sensors 18 include devices, modules, or subsystems whose purpose is to detect events or changes in an environment and send the information (e.g., sensor data) about the detected events to some other device, module, subsystem, etc., such as the controller 12. Examples of such sensors 18 include, inter alia, inertia measurement units (IMU) comprising accelerometers, gyroscopes, and/or magnetometers; microelectromechanical systems (MEMS) or nanoelectromechanical systems (NEMS) comprising 3-axis accelerometers, 3-axis gyroscopes and/or magnetometers, level sensors, flow sensors, temperature sensors (e.g., thermistors), pressure sensors, barometric pressure sensors, gravimeters, altimeters, image capture devices (e.g., cameras), light detection and ranging (LiDAR) sensors, proximity sensors (e.g., infrared radiation detector and the like), depth sensors, ambient light sensors, ultrasonic transceivers; microphones; etc. In embodiments, the electronic nanodevices/chips of the present disclosure may be considered sensors, in that they are designed to sense biomolecule translocation/mounting/linking events of biomolecules, where such information may be in turn relayed to controller 12 and/or to some other device, module, subsystem, etc.

The actuators 21 are devices, modules, or subsystems that change a state, position, and/or orientation, or move or control a mechanism or system, including external mechanisms/systems or the actuator(s) 21 themselves. The actuators 21 comprise electrical and/or mechanical elements that convert energy (e.g., electric current, moving air and/or liquid, etc.) into some kind of motion. The actuators 21 may be or include one or more electronic (or electrochemical) devices, such as piezoelectric biomorphs, solid state actuators, solid state relays (SSRs), shape-memory alloy-based actuators, electroactive polymer-based actuators, relay driver integrated circuits (ICs), and/or the like. The actuators 21 may be or include one or more electromechanical devices such as pneumatic actuators, hydraulic actuators, electro-hydrostatic actuators (EHA), electromechanical switches including electromechanical relays (EMRs), motors (e.g., DC motors, stepper motors, servomechanisms, linear motors, linear drives, etc.), and/or the like. The actuators 21 may be coupled with, and control the motion of other devices, such as valves, vacuum generators (e.g., venturi-based ejectors, blowers, etc.) pumps (e.g., vacuum pumps, suction pumps, hydraulic pumps, compressors, etc.), gears, wheels, thrusters, propellers, claws, clamps, hooks, an audible sound generator, and/or the like.

The signaling means (not shown) may include any element or combination of elements for conveying information/instructions to components of the control system 14. In some embodiments, the signaling means is or includes a suitable bus or interconnect (IX) technology, such as Peripheral Component Interconnect (PCI), PCI express (PCIe), industry standard architecture (ISA), Universal Serial Bus (USB), HyperTransport interconnect, Time-Triggered Protocol (TTP), FieldBus (e.g., IEC 61158) based IX such as PROFIBUS, Modbus, Common Industrial Protocol (CIP) IX, EtherNet Industrial Protocol (EtherNetIP), and the like. In some embodiments, the signaling means is or includes one or more network interface controllers that connect the controller 12 to other components/devices using a physical connection, which may be electrical (e.g., a "copper interconnect") or optical, and which operates according to a wired network protocol such as Ethernet, Industrial Ethernet, Ethernet over USB, Controller Area Network (CAN), Local Interconnect Network (LIN), PROFINET, among many others. In some embodiments, the signaling means is or includes a radiofrequency transmitter (and receiver) or transceiver configured to enable communication with or over wireless networks using modulated electromagnetic radiation through a non-solid medium (e.g., over an air interface).

The embodiment shown at FIG. 9 also includes robotic system 20, and electronic nanodevices and/or chips 25 of the present disclosure. In embodiments, robotics system 20 may be comprised of or may comprise a fluidics device/system, such as a microfluidics device/system. Broadly speaking, robotic system 20 may be comprised of machinery capable of, in an automated fashion, delivering one or more samples, for example to wells of the multiwell structures (e.g., top multiwell structure 810 at FIG. 8). For example, robotic system 20 may be comprised of one or more multichannel pipettes, tubing, vacuum and/or pressure source, moveable arms, microfluidics delivery channels, and the like, to enable a sample to be acquired from one location and delivered/provided to one or more wells associated with the multiwell structures as herein disclosed. In some examples, robotic system 20 may be capable of manipulating electronic devices and/or chips of the present disclosure, for example to place an electronic device and/or chip in a desired location for subsequent use, to couple or decouple multiwell structures (e.g., top multiwell structure 810 and/or bottom multiwell structure 815) with corresponding chips, and the like.

In embodiments, robotic system 20 may additionally or alternatively include other componentry, such as a microscope capable of automatically being adjusted in response to instructions received from controller 12. In embodiments, such a microscope is a TERS microscope.

In embodiments, controller 12 may be capable of sending and/or receiving electrical and/or optical signals to/from electronic nanodevices and/or chips 25. For example, the controller may be capable of sending and receiving signals for feedback control of electrochemical deposition of electrodes associated with said electronic nanodevices and/or chips 25, and may additionally or alternatively be capable of acquiring data pertaining to individual translocation and/or mounting/linking events of individual molecules corresponding to any number of electronic nanodevices included as part of electronic nanodevices/chips 25. For example, the controller 12 may retrieve data corresponding to ionic conductance and/or tunneling conductance associated with single molecule translocation/linking/mounting events. In the case of optical signals, it may be understood that robotic system 20 may be configured to collect optical data by way of the microscope associated with the robotic system, in some embodiments, and to send the data to the controller 12 for further processing.

Thus, broadly speaking, controller 12 may be configured to send and receive information (e.g., electronic signals) to/from robotic system 20, robotic system 20 may be capable of sending and receiving information to/from controller 12 and/or to/from electronic nanodevices/chips 25, and electronic nanodevices/chips 25 may be capable of sending and receiving information to/from robotic system 20 and/or to/from controller 12. This is illustratively depicted by arrows 910.

In some embodiments of the present disclosure, there is provided an electronic device, including: a top fluidic channel/chamber and a bottom fluidic channel/chamber fabricated in a planar substrate, the top fluidic channel/chamber being sealed at a bottom of the electronic device and including a first open window at a top of the electronic device, and the bottom fluidic channel/chamber being sealed at the top of the electronic device and including a second open window at the bottom of the electronic device; a first electrode and a second electrode positioned in a space of the electronic device between the top fluidic channel/chamber and the bottom fluidic channel/chamber; and a nanogap having dimensions defined in part by a distance between the first electrode and the second electrode, the nanogap having a single path for a molecule to travel from the top fluidic channel/chamber to the bottom fluidic channel/chamber and/or from the bottom fluidic channel/chamber to the top fluidic channel/chamber, wherein the distance is between about 1-100 nm, and wherein the nanogap is self-aligned and has a narrowest bottleneck in the single path between the top fluidic channel/chamber and the bottom fluidic channel.

In some embodiments, the distance is defined via the first and the second electrodes being electrochemically deposited under feedback control with one or more metal materials within the top fluidic channel/chamber and/or the bottom fluidic channel/chamber, thereby forming the single path.

In some embodiments, the planar substrate is a transparent substrate.

In some embodiments, the transparent substrate is glass or quartz.

In some embodiments, the planar substrate is a non-transparent substrate.

In some embodiments, the planar substrate is silicon coated with SiO2 and/or Si3N4.

In some embodiments, the first electrode and the second electrode are formed of gold, palladium, platinum, or another metal or alloy compatible with top-down lithography and electrochemical deposition, or combinations thereof.

In some embodiments, the space in which the first electrode and the second electrode are positioned is formed at least in part by one or more dielectric layers.

In some embodiments, the one or more dielectric layers is HfO2, ZrO2, SiO2, Si3N4, or a combination thereof.

In some embodiments, the electronic device further includes an additional layer of polymer dielectric for sealing.

In some embodiments, the additional layer of polymer dielectric includes one or more of SU-8 polymer and parylene.

In some embodiments, the one or more dielectric layers with or without the additional layer of polymer dielectric is about 100 nm to about 100 µm.

In some embodiments, the one or more metal materials are Ni, Co, gold, palladium, platinum, iridium, alloys thereof or combinations thereof.

In some embodiments, the first and second electrodes being electrochemically deposited with the one or more metal materials under feed-back control further includes a pulsed electrochemical deposition operation with a pulse width of 50 ms or less and a rest period of between about 500 ms and 2 seconds between pulses.

In some embodiments, the molecule is DNA.

In some embodiments of the present disclosure, there is provided a method to measure electronic and/or optical properties from one or more molecules, the method including: detecting, with an electronic device, of an individual mounting and/or translocation event of the one or more molecules by correlating an ionic current between the top fluidic channel/chamber and the bottom fluidic channel/chamber, and a tunneling current between the first and second electrodes through the nanogap; and performing electrical and/or optical characterization of at least one of the one or more molecules.

In some embodiments, the planar substrate is a transparent substrate, and wherein the performing electrical and/or optical characterization includes performing Raman spectroscopy by performing tip-enhanced Raman spectroscopy through the transparent substrate to characterize a dynamic structure of the at least one of the one or more molecules.

In some embodiments, the performing electrical and/or optical characterization includes determining a sequence corresponding to the at least one of the one or more molecules.

In some embodiments of the present disclosure, there is provided a chip for measuring electrical and/or optical properties from one or more molecules, including: a plurality of electronic devices.

In some embodiments, the number of the plurality of electronic devices is between 2-1000.

In some embodiments, the number of the plurality of electronic devices is between 1000-10,000.

In some embodiments, the number of the plurality of electronic devices is greater than 10,000.

In some embodiments, the plurality of electronic devices are divided into a set number of different groups.

In some embodiments, the chip further includes one or more multiwell structures coupled to the chip, with individual wells of the one or more multiwell structures corresponding to each of the set number of different groups.

In some embodiments, the chip further includes one or more multiplexers for collecting signals from electronic devices corresponding to each of the set number of different groups.

In some embodiments, the one or more multiwell structures further includes a first multiwell structure that couples to a top-side of the chip for providing samples to the top fluidic channel/chamber of each of the plurality of electronic devices; and/or a second multiwell structure that couples to a bottom-side of the chip for receiving the samples provided to the top fluidic channel/chamber following translocation of an analyte within each of the samples to the bottom fluidic channel/chamber.

In some embodiments of the present disclosure, there is provided a system for high-throughput analysis of single molecules, including: a chip; a fluidics device capable of delivering individual samples to each of the set number of different groups; and a controller for storing instructions in non-transitory memory that, when executed, cause the controller to: instruct the fluidics device to provide individual samples to one or more of the set number of different groups; and following the providing of individual samples, record data including one or more of ionic current between the top fluidic channel/chamber and the bottom fluidic channel/chamber, tunneling current between the first electrode and the second electrode, and an optical signal from each electronic device of the set number of different groups, the data corresponding to individual mounting and/or translocation events of individual molecules within the electronic devices of the set number of different groups.

In some embodiments of the present disclosure, there is provided a method of making an electronic device that includes a nanopore and a tunneling junction, the method including: depositing onto a substrate layer a first sacrificial layer for defining a final cavity for electrochemical deposition; depositing onto the substrate layer a second outer sacrificial layer for defining a top fluidic channel/chamber and a bottom fluidic channel/chamber on two sides of the final cavity; positioning a pair of electrodes with a spacing of about 200 nm to 2 μm on top of the first sacrificial layer; depositing a passivation layer on top of the pair of electrodes, the first sacrificial layer, the second outer sacrificial layer, and the substrate layer; and conducting a dry etching process to remove a section of the passivation layer and to remove a section of the substrate layer from a bottom-side of the substrate layer, thereby respectively providing a first window to the second outer sacrificial layer corresponding the top fluidic channel/chamber, and a second window to the second outer sacrificial layer corresponding to the bottom fluidic channel/chamber.

In some embodiments, the method further includes: chemically etching the first and second sacrificial layers to provide the final cavity, the top fluidic channel/chamber, and the bottom fluidic channel/chamber; and narrowing the spacing between the pair of electrodes by a process of controlled electrochemical deposition of a metal onto the pair of electrodes to form the nanopore and the tunneling junction.

In some embodiments, the first sacrificial layer includes one or more of chromium, nickel, magnesium, and aluminum.

In some embodiments, the first sacrificial layer is of a thickness between 1-100 nm.

In some embodiments, the first sacrificial layer is of dimensions corresponding to about 10 μm×10 μm.

In some embodiments, the second outer sacrificial layer includes one or more of aluminum, magnesium, chromium, and nickel.

In some embodiments, the second outer sacrificial layer is about 100-500 nm in thickness.

In some embodiments, the process of controlled electrodeposition further includes: conducting a pulsed electrochemical deposition operation including a pulse width of 50 ms or less and a rest period of between about 500 ms and 2 seconds between pulses.

In some embodiments, the pulse width is between 1 ms and 5 ms.

In some embodiments, the pulse width is between 1 μs and 500 μs.

In some embodiments, the pair of electrodes include gold, platinum, palladium, or another noble metal or alloy compatible with top-down lithography and electrochemical deposition.

In some embodiments, the metal used to narrow the spacing between the pair of electrodes is nickel, cobalt, gold, palladium, platinum, iridium, an alloy thereof, or combinations thereof.

In some embodiments, the narrowing the spacing between the pair of electrodes by the process of controlled electrodeposition further includes: providing the metal in just one of the top fluidic channel/chamber and the bottom fluidic channel/chamber.

In some embodiments, the narrowing the spacing between the pair of electrodes by the process of controlled electrodeposition further includes: repeatedly narrowing and then expanding the spacing between the pair of electrodes a set number of times via repetitive reversing of a polarity of the pair of electrodes.

In some embodiments, the narrowing the spacing between the pair of electrodes by the process of controlled electrodeposition is used to create a final spacing between the pair of electrodes of 1 nm to 100 nm.

In some embodiments, the final spacing is between 1 nm to 20 nm.

In some embodiments, the final spacing is between 1-2 nm.

In some embodiments, the passivation layer includes one or more layers of dielectrics, each including one or more of $HfO_2$, $ZrO_2$, $SiO_2$, and $Si_3N_4$. In some embodiments, the passivation layer is further sealed with an additional layer of one or more of SU-8 polymer, parylene, and other polymer dielectrics.

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

Clauses

Some embodiments of the present disclosure have features as described in the clauses below.

1. An electronic device, comprising:
    a top fluidic channel/chamber and a bottom fluidic channel/chamber fabricated in a planar substrate, the top fluidic channel/chamber being sealed at a bottom of the electronic device and including a first open window at a top of the electronic device, and the bottom fluidic channel/chamber being sealed at the top of the electronic device and including a second open window at the bottom of the electronic device;
    a first electrode and a second electrode positioned in a space of the electronic device between the top fluidic channel/chamber and the bottom fluidic channel/chamber; and
    a nanogap having dimensions defined in part by a distance between the first electrode and the second electrode, the nanogap having a single path for a molecule to travel from the top fluidic channel/chamber to the bottom fluidic channel/chamber and/or from the bottom fluidic channel/chamber to the top fluidic channel/chamber, wherein the distance is between about 1-100 nm, and wherein the nanogap is self-aligned and has a narrowest bottleneck in the single path between the top fluidic channel/chamber and the bottom fluidic channel.

2. The electronic device of clause 1, wherein the distance is defined via the first and the second electrodes being electrochemically deposited under feedback control with one or more metal materials within the top fluidic channel/chamber and/or the bottom fluidic channel/chamber, thereby forming the single path.

3. The electronic device of clause 2, wherein the planar substrate is a transparent substrate.

4. The electronic device of clause 3, wherein the transparent substrate is glass or quartz.

5. The electronic device of clause 2, wherein the planar substrate is a non-transparent substrate.

6. The electronic device of clause 5, wherein the planar substrate is silicon coated with $SiO_2$ and/or $Si_3N_4$.

7. The device of any one of clauses 2-6, wherein the first electrode and the second electrode are formed of gold, palladium, platinum, or another metal or alloy compatible with top-down lithography and electrochemical deposition, or combinations thereof.

8. The electronic device of any one of clauses 2-7, wherein the space in which the first electrode and the second electrode are positioned is formed at least in part by one or more dielectric layers.

9. The electronic device of clause 8, wherein the one or more dielectric layers is $HfO_2$, $ZrO_2$, $SiO_2$, $Si_3N_4$, or a combination thereof.

10. The electronic device of clause 8 or clause 9, further comprising an additional layer of polymer dielectric for sealing.

11. The electronic device of clause 10, wherein the additional layer of polymer dielectric comprises one or more of SU-8 polymer and parylene.

12. The electronic device of any one of clauses 8-11, wherein the one or more dielectric layers with or without the additional layer of polymer dielectric is about 100 nm to about 100 µm.

13. The electronic device of any one of clauses 2-12, wherein the one or more metal materials are Ni, Co, gold, palladium, platinum, iridium, alloys thereof or combinations thereof.

14. The electronic device of clause 13, wherein the first and second electrodes being electrochemically deposited with the one or more metal materials under feed-back control further comprises a pulsed electrochemical deposition operation with a pulse width of 50 ms or less and a rest period of between about 500 ms and 2 seconds between pulses.

15. The electronic device of any one of clauses 2-14, wherein the molecule is DNA.

16. A method to measure electronic and/or optical properties from one or more molecules, the method comprising:
    detecting with the electronic device of any one of clauses 2-15 of an individual mounting and/or translocation event of the one or more molecules by correlating an ionic current between the top fluidic channel/chamber and the bottom fluidic channel/chamber, and a tunneling current between the first and second electrodes through the nanogap; and
    performing electrical and/or optical characterization of at least one of the one or more molecules.

17. The method of clause 16, wherein the planar substrate is a transparent substrate, and wherein the performing electrical and/or optical characterization includes performing Raman spectroscopy by performing tip-enhanced Raman spectroscopy through the transparent substrate to characterize a dynamic structure of the at least one of the one or more molecules.

18. The method of clause 16, wherein the performing electrical and/or optical characterization includes determining a sequence corresponding to the at least one of the one or more molecules.

19. A chip for measuring electrical and/or optical properties from one or more molecules, comprising:
    a plurality of the electronic devices, each being the electronic device of any one of clauses 2-15.

20. The chip of clause 19, wherein the number of the plurality of electronic devices is between 2-1000.

21. The chip of clause 19, wherein the number of the plurality of electronic devices is between 1000-10,000.

22. The chip of clause 19, wherein the number of the plurality of electronic devices is greater than 10,000.

23. The chip of any one of clauses 19-22, wherein the plurality of electronic devices are divided into a set number of different groups.

24. The chip of clause 23, further comprising one or more multiwell structures coupled to the chip, with individual wells of the one or more multiwell structures corresponding to each of the set number of different groups.

25. The chip of any one of clauses 23-24, further comprising one or more multiplexers for collecting signals from electronic devices corresponding to each of the set number of different groups.

26. The chip of any one of clauses 23-25, wherein the one or more multiwell structures further comprises a first multiwell structure that couples to a top-side of the chip for providing samples to the top fluidic channel/chamber of each of the plurality of electronic devices; and/or
    a second multiwell structure that couples to a bottom-side of the chip for receiving the samples provided to the top fluidic channel/chamber following translocation of an analyte within each of the samples to the bottom fluidic channel/chamber.

27. A system for high-throughput analysis of single molecules, comprising:
    the chip of any one of clauses 23-26;
    a fluidics device capable of delivering individual samples to each of the set number of different groups; and
    a controller for storing instructions in non-transitory memory that, when executed, cause the controller to:
        instruct the fluidics device to provide individual samples to one or more of the set number of different groups; and
        following the providing of individual samples, record data comprising one or more of ionic current between the top fluidic channel/chamber and the bottom fluidic channel/chamber, tunneling current between the first electrode and the second electrode, and an optical signal from each electronic device of the set number of different groups, the data corresponding to individual mounting and/or translocation events of individual molecules within the electronic devices of the set number of different groups.

28. A method of making an electronic device that includes a nanopore and a tunneling junction, the method comprising:
    depositing onto a substrate layer a first sacrificial layer for defining a final cavity for electrochemical deposition;
    depositing onto the substrate layer a second outer sacrificial layer for defining a top fluidic channel/chamber and a bottom fluidic channel/chamber on two sides of the final cavity;
    positioning a pair of electrodes with a spacing of about 200 nm to 2 µm on top of the first sacrificial layer;
    depositing a passivation layer on top of the pair of electrodes, the first sacrificial layer, the second outer sacrificial layer, and the substrate layer; and
    conducting a dry etching process to remove a section of the passivation layer and to remove a section of the substrate layer from a bottom-side of the substrate layer, thereby respectively providing a first window to the second outer sacrificial layer corresponding the top fluidic channel/chamber, and a second window to the second outer sacrificial layer corresponding to the bottom fluidic channel/chamber.

29. The method of clause 28, further comprising:
chemically etching the first and second sacrificial layers to provide the final cavity, the top fluidic channel/chamber, and the bottom fluidic channel/chamber; and
narrowing the spacing between the pair of electrodes by a process of controlled electrochemical deposition of a metal onto the pair of electrodes to form the nanopore and the tunneling junction.

30. The method of clause 29, wherein the first sacrificial layer comprises one or more of chromium, nickel, magnesium, and aluminum.

31. The method of any one of clauses 28-30, wherein the first sacrificial layer is of a thickness between 1-100 nm.

32. The method of any one of clauses 28-31, wherein the first sacrificial layer is of dimensions corresponding to about 10 μm×10 μm.

33. The method of any one of clauses 28-32, wherein the second outer sacrificial layer comprises one or more of aluminum, magnesium, chromium, and nickel.

34. The method of any one of clauses 28-33, wherein the second outer sacrificial layer is about 100-500 nm in thickness.

35. The method of any one of clauses 29-34, wherein the process of controlled electrodeposition further comprises:
conducting a pulsed electrochemical deposition operation comprising a pulse width of 50 ms or less and a rest period of between about 500 ms and 2 seconds between pulses.

36. The method of clause 35, wherein the pulse width is between 1 ms and 5 ms.

37. The method of clause 35 wherein the pulse width is between 1 μs and 500 μs.

38. The method of any one of clauses 28-37, wherein the pair of electrodes comprise gold, platinum, palladium, or another noble metal or alloy compatible with top-down lithography and electrochemical deposition.

39. The method of any one of clauses 28-38, wherein the metal used to narrow the spacing between the pair of electrodes is nickel, cobalt, gold, palladium, platinum, iridium, an alloy thereof, or combinations thereof.

40. The method of any one of clauses 29-39, wherein the narrowing the spacing between the pair of electrodes by the process of controlled electrodeposition further comprises:
providing the metal in just one of the top fluidic channel/chamber and the bottom fluidic channel/chamber.

41. The method of any one of clauses 29-40, wherein the narrowing the spacing between the pair of electrodes by the process of controlled electrodeposition further comprises:
repeatedly narrowing and then expanding the spacing between the pair of electrodes a set number of times via repetitive reversing of a polarity of the electrochemical potential applied to the pair of electrodes.

42. The method of any one of clauses 29-41, wherein the narrowing the spacing between the pair of electrodes by the process of controlled electrodeposition is used to create a final spacing between the pair of electrodes of 1 nm to 100 nm.

43. The method of clause 42, wherein the final spacing is between 1 nm to 20 nm.

44. The method of clause 43, wherein the final spacing is between 1-2 nm.

45. The method of any one of clauses 28-44, wherein the passivation layer comprises one or more layers of dielectrics, each comprising one or more of $HfO_2$, $ZrO_2$, $SiO_2$, and $Si_3N_4$.

46. The method of clause 45, wherein the passivation layer is further sealed with an additional layer of one or more of SU-8 polymer, parylene, and other polymer dielectrics.

47. A device, a system including the device, a method of making the device, a method of making the system, a method of using the device, or a method of using the system, the device being for: delivering molecules between tunable metal nanogaps, linking molecules between the tunable metal nanogaps, and/or measuring electrical and optical properties allowing for single molecule detection, as substantially disclosed and described in the specification and figures herein.

What is claimed is:

1. A chip for measuring electrical and/or optical properties from one or more molecules, comprising:
a plurality of electronic devices, each of the plurality of electronic devices comprising:
a top fluidic channel/chamber and a bottom fluidic channel/chamber fabricated in a planar substrate, the top fluidic channel/chamber being sealed at a bottom of the electronic device and including a first open window at a top of the electronic device, and the bottom fluidic channel/chamber being sealed at the top of the electronic device and including a second open window at the bottom of the electronic device,
a first electrode and a second electrode positioned in a space of the electronic device between the top fluidic channel/chamber and the bottom fluidic channel/chamber, and
a nanogap having dimensions defined in part by a distance between the first electrode and the second electrode, the nanogap having a single path for a molecule to travel from the top fluidic channel/chamber to the bottom fluidic channel/chamber and/or from the bottom fluidic channel/chamber to the top fluidic channel/chamber,
wherein the distance is between about 1-100 nm, and wherein the nanogap has a narrowest bottleneck in the single path between the top fluidic channel/chamber and the bottom fluidic channel,
wherein the plurality of electronic devices are divided into a set number of different groups, and
wherein the chip further comprises one or more multiwell structures coupled to the chip, with individual wells of the one or more multiwell structures corresponding to each of the set number of different groups.

2. The chip of claim 1, wherein, for a first electronic device of the plurality of electronic devices, the distance is defined via the first and the second electrodes being electrochemically deposited under feedback control with one or more metal materials within the top fluidic channel/chamber and/or the bottom fluidic channel/chamber, thereby forming the single path.

3. The chip of claim 2, wherein, for the first electronic device, the planar substrate is a transparent substrate.

4. The chip of claim 3, wherein, for the first electronic device, the transparent substrate is glass or quartz.

5. The chip of claim 2, wherein, for the first electronic device, the planar substrate is a non-transparent substrate.

6. The chip of claim 5, wherein, for the first electronic device, the planar substrate is silicon coated with $SiO_2$ and/or $Si_3N_4$.

7. The chip of claim 2, wherein, for the first electronic device, the first electrode and the second electrode are formed of gold, palladium, platinum, or another noble metal or alloy compatible with top-down lithography and electrochemical deposition, or combinations thereof.

8. The chip of claim 2, wherein, for the first electronic device, the space in which the first electrode and the second electrode are positioned is formed at least in part by one or more dielectric layers.

9. The chip of claim 8, wherein, for the first electronic device, the one or more dielectric layers is $HfO_2$, $ZrO_2$, $SiO_2$, $Si_3N_4$, or a combination thereof.

10. The chip of claim 8, further comprising wherein the first electronic device further comprises an additional layer of polymer dielectric for sealing.

11. The chip of claim 10, wherein, for the first electronic device, the additional layer of polymer dielectric comprises one or more of SU-8 polymer and parylene.

12. The chip of claim 11, wherein, for the first electronic device, the one or more dielectric layers with or without the additional layer of polymer dielectric is about 100 nm to about 100 μm.

13. The chip of claim 2, wherein, for the first electronic device, the one or more metal materials are Ni, Co, gold, palladium, platinum, iridium, alloys thereof or combinations thereof.

14. The chip of claim 13, wherein, for the first electronic device, the first and second electrodes being electrochemically deposited with the one or more metal materials under feed-back control further comprises a pulsed electrochemical deposition operation with a pulse width of 50 ms or less and a rest period of between about 500 ms and 2 seconds between pulses.

15. The chip of claim 2, wherein the molecule is DNA.

16. The chip of claim 1, wherein, for a first electronic device of the plurality of electronic devices, the nanogap is self-aligned.

17. The chip of claim 1, wherein the number of the plurality of electronic devices is between 2-1000.

18. The chip of claim 1, wherein the number of the plurality of electronic devices is between 1000-10,000.

19. The chip of claim 1, wherein the number of the plurality of electronic devices is greater than 10,000.

20. The chip of claim 1, wherein the one or more multiwell structures further comprises a first multiwell structure that couples to a top-side of the chip for providing samples to the top fluidic channel/chamber of each of the plurality of electronic devices; and/or a second multiwell structure that couples to a bottom-side of the chip for receiving the samples provided to the top fluidic channel/chamber following translocation of an analyte within each of the samples to the bottom fluidic channel/chamber.

21. A method, using an electronic device, to measure electronic and/or optical properties from one or more molecules, the electronic device comprising:
a top fluidic channel/chamber and a bottom fluidic channel/chamber fabricated in a planar substrate, the top fluidic channel/chamber being sealed at a bottom of the electronic device and including a first open window at a top of the electronic device, and the bottom fluidic channel/chamber being sealed at the top of the electronic device and including a second open window at the bottom of the electronic device;
a first electrode and a second electrode positioned in a space of the electronic device between the top fluidic channel/chamber and the bottom fluidic channel/chamber; and
a nanogap having dimensions defined in part by a distance between the first electrode and the second electrode, the nanogap having a single path for a molecule to travel from the top fluidic channel/chamber to the bottom fluidic channel/chamber and/or from the bottom fluidic channel/chamber to the top fluidic channel/chamber,
wherein the distance is between about 1-100 nm, and wherein the nanogap has a narrowest bottleneck in the single path between the top fluidic channel/chamber and the bottom fluidic channel,
wherein the method comprises:
detecting with the electronic device of an individual mounting and/or translocation event of the one or more molecules by correlating an ionic current between the top fluidic channel/chamber and the bottom fluidic channel/chamber, and a tunneling current between the first and second electrodes through the nanogap; and
performing electrical and/or optical characterization of at least one of the one or more molecules,
wherein the planar substrate is a transparent substrate, and
wherein the performing electrical and/or optical characterization includes performing Raman spectroscopy by performing tip-enhanced Raman spectroscopy through the transparent substrate to characterize a dynamic structure of the at least one of the one or more molecules.

22. The method of claim 21, wherein the performing electrical and/or optical characterization includes determining a sequence corresponding to the at least one of the one or more molecules.

23. The method of claim 21, wherein the distance is defined via the first and the second electrodes being electrochemically deposited under feedback control with one or more metal materials within the top fluidic channel/chamber and/or the bottom fluidic channel/chamber, thereby forming the single path.

24. A chip for measuring electrical and/or optical properties from one or more molecules, comprising:
a plurality of electronic devices, each of the plurality of electronic devices comprising:
a top fluidic channel/chamber and a bottom fluidic channel/chamber fabricated in a planar substrate, the top fluidic channel/chamber being sealed at a bottom of the electronic device and including a first open window at a top of the electronic device, and the bottom fluidic channel/chamber being sealed at the top of the electronic device and including a second open window at the bottom of the electronic device,
a first electrode and a second electrode positioned in a space of the electronic device between the top fluidic channel/chamber and the bottom fluidic channel/chamber, and
a nanogap having dimensions defined in part by a distance between the first electrode and the second electrode, the nanogap having a single path for a molecule to travel from the top fluidic channel/chamber to the bottom fluidic channel/chamber and/or from the bottom fluidic channel/chamber to the top fluidic channel/chamber,
wherein the distance is between about 1-100 nm, and wherein the nanogap has a narrowest bottleneck in the single path between the top fluidic channel/chamber and the bottom fluidic channel,
wherein the plurality of electronic devices are divided into a set number of different groups, and
wherein the chip further comprises one or more multiplexers for collecting signals from electronic devices corresponding to each of the set number of different groups.

25. The chip of claim 24, wherein, for a first electronic device of the plurality of electronic devices, the distance is defined via the first and the second electrodes being electrochemically deposited under feedback control with one or more metal materials within the top fluidic channel/chamber and/or the bottom fluidic channel/chamber, thereby forming the single path.

26. A system for high-throughput analysis of single molecules, comprising:
a chip for measuring electrical and/or optical properties from one or more molecules, the chip comprising:
a plurality of electronic devices, each of the plurality of electronic devices comprising:
a top fluidic channel/chamber and a bottom fluidic channel/chamber fabricated in a planar substrate, the top fluidic channel/chamber being sealed at a bottom of the electronic device and including a first open window at a top of the electronic device, and the bottom fluidic channel/chamber being sealed at the top of the electronic device and including a second open window at the bottom of the electronic device,
a first electrode and a second electrode positioned in a space of the electronic device between the top fluidic channel/chamber and the bottom fluidic channel/chamber, and
a nanogap having dimensions defined in part by a distance between the first electrode and the second electrode, the nanogap having a single path for a molecule to travel from the top fluidic channel/chamber to the bottom fluidic channel/chamber and/or from the bottom fluidic channel/chamber to the top fluidic channel/chamber,
wherein the distance is between about 1-100 nm, and wherein the nanogap has a narrowest bottleneck in the single path between the top fluidic channel/chamber and the bottom fluidic channel, and
wherein the plurality of electronic devices are divided into a set number of different groups;
a fluidics device capable of delivering individual samples to each of the set number of different groups; and
a controller for storing instructions in non-transitory memory that, when executed, cause the controller to:
instruct the fluidics device to provide individual samples to one or more of the set number of different groups; and
following the providing of individual samples, record data comprising one or more of ionic current between the top fluidic channel/chamber and the bottom fluidic channel/chamber, tunneling current between the first electrode and the second electrode, and an optical signal from each electronic device of the set number of different groups, the data corresponding to individual mounting and/or translocation events of individual molecules within the electronic devices of the set number of different groups.

27. The system of claim 26, wherein, for a first electronic device of the plurality of electronic devices, the distance is defined via the first and the second electrodes being electrochemically deposited under feedback control with one or more metal materials within the top fluidic channel/chamber and/or the bottom fluidic channel/chamber, thereby forming the single path.

* * * * *